United States Patent [19]
Hinchliffe et al.

[11] Patent Number: 5,813,977
[45] Date of Patent: Sep. 29, 1998

[54] SURGICAL HAND SUPPORT APPARATUS

[75] Inventors: Peter W. J. Hinchliffe, New Haven; Dawn J. Pappalardo, Fairfield; Scott Larsen, Newtown; Ian J. Tovey, Milford; Christopher McDonnell, Newtown, all of Conn.

[73] Assignee: United States Surgical Corporation, Norwalk, Conn.

[21] Appl. No.: 696,418

[22] Filed: Aug. 13, 1996

Related U.S. Application Data

[62] Division of Ser. No. 319,853, Oct. 7, 1994, Pat. No. 5,547,463.

[51] Int. Cl.[6] .................................................. A61B 1/06
[52] U.S. Cl. ........................ 600/183; 602/20; 600/102; 128/898; 606/192
[58] Field of Search ..................... 602/20, 21, 22; 600/102, 163; 128/845, 846, 869, 877, 878, 679, 898; 5/621, 623, 646, 647; 606/192, 198, 167

[56] References Cited

U.S. PATENT DOCUMENTS

| | | |
|---|---|---|
| 2,266,231 | 12/1941 | Mazzo . |
| 2,357,233 | 9/1944 | Goldberg . |
| 3,476,108 | 11/1969 | Matakas . |
| 3,540,719 | 11/1970 | Lomneg . |
| 3,746,332 | 7/1973 | Hakstian . |
| 3,762,401 | 10/1973 | Tupper . |
| 3,769,970 | 11/1973 | Swanson . |
| 3,901,227 | 8/1975 | Kaltskin . |
| 4,082,257 | 4/1978 | Strickland . |
| 4,204,533 | 5/1980 | Forster et al. . |
| 4,220,334 | 9/1980 | Kanamoto et al. . |
| 4,252,306 | 2/1981 | Johnson et al. . |
| 4,265,232 | 5/1981 | Stonich . |
| 4,370,976 | 2/1983 | Wanchik et al. . |
| 4,453,933 | 6/1984 | Speaker . |
| 4,456,002 | 6/1984 | Barber et al. . |
| 4,672,955 | 6/1987 | Cooper . |
| 4,674,110 | 6/1987 | Eaton et al. . |
| 4,766,892 | 8/1988 | Kreitman . |
| 4,781,178 | 11/1988 | Gordon . |
| 4,840,168 | 6/1989 | Lonardo . |
| 4,850,341 | 7/1989 | Fabry et al. . |
| 4,883,073 | 11/1989 | Aziz . |
| 4,909,264 | 3/1990 | Wadsworth, III et al. . |
| 4,941,460 | 7/1990 | Working . |
| 4,941,480 | 7/1990 | McClean et al. . |
| 4,982,744 | 1/1991 | Stanec . |
| 5,025,801 | 6/1991 | Callaway . |
| 5,029,573 | 7/1991 | Chow . |
| 5,074,291 | 12/1991 | Carter . |
| 5,136,743 | 8/1992 | Pirela-Cruz . |
| 5,140,998 | 8/1992 | Vickers . |
| 5,179,963 | 1/1993 | Berger .............................. 606/192 X |
| 5,203,766 | 4/1993 | Carter et al. . |
| 5,256,136 | 10/1993 | Sucher . |
| 5,329,941 | 7/1994 | Bodine . |
| 5,331,975 | 7/1994 | Bonutti ............................. 606/192 X |
| 5,372,145 | 12/1994 | Berger ................................... 128/878 |
| 5,425,355 | 6/1995 | Killick .................................. 600/183 |

FOREIGN PATENT DOCUMENTS

| | | |
|---|---|---|
| 0 552 980 A1 | 7/1993 | European Pat. Off. . |
| 2088216 | 6/1982 | United Kingdom . |
| WO 86/01711 | 3/1986 | WIPO . |
| WO 94/06378 | 3/1994 | WIPO . |

*Primary Examiner*—Beverly M. Flanagan

[57] ABSTRACT

A surgical hand support apparatus includes a support member having a supporting surface for supporting at least the hand of a patient, a finger restraining member moveable relative to the supporting surface to be positioned to engage the fingers of the patient and a thumb restraining member moveable relative to the supporting surface to be positioned to engage the thumb of the patient. A quick release mechanism is associated with the finger restraining member and the thumb restraining member to lock the respective members at predetermined positions relative to the supporting surface. The apparatus may also include a wrist restraining member to engage the patient's wrist. An instrument support member is associated with the wrist restraining member and is configured to support a surgical instrument. A method is also disclosed for performing carpal tunnel surgery wherein the patient's hand is held in the hand support and a guiding instrument and balloon catheter are inserted through the instrument support member.

12 Claims, 20 Drawing Sheets

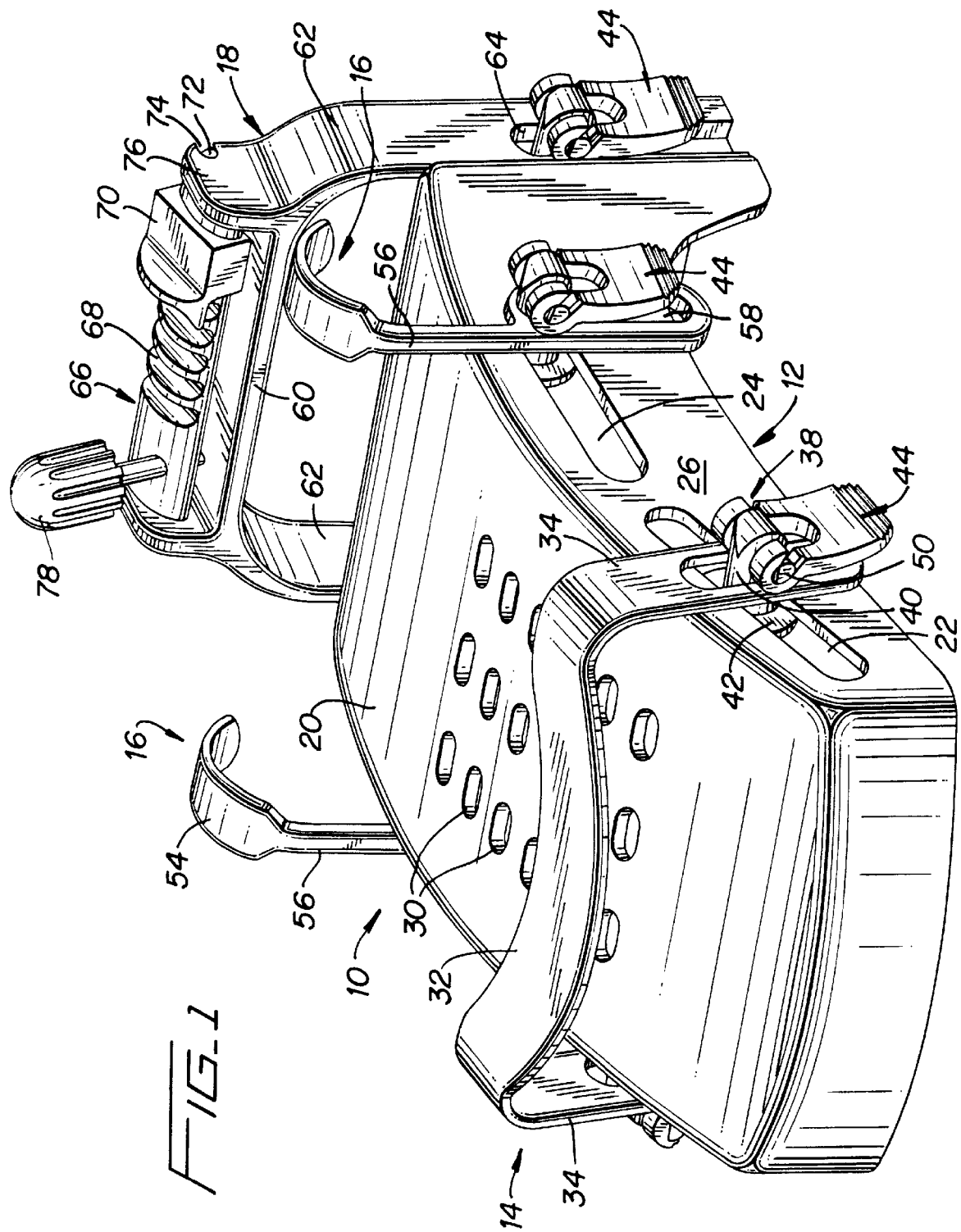

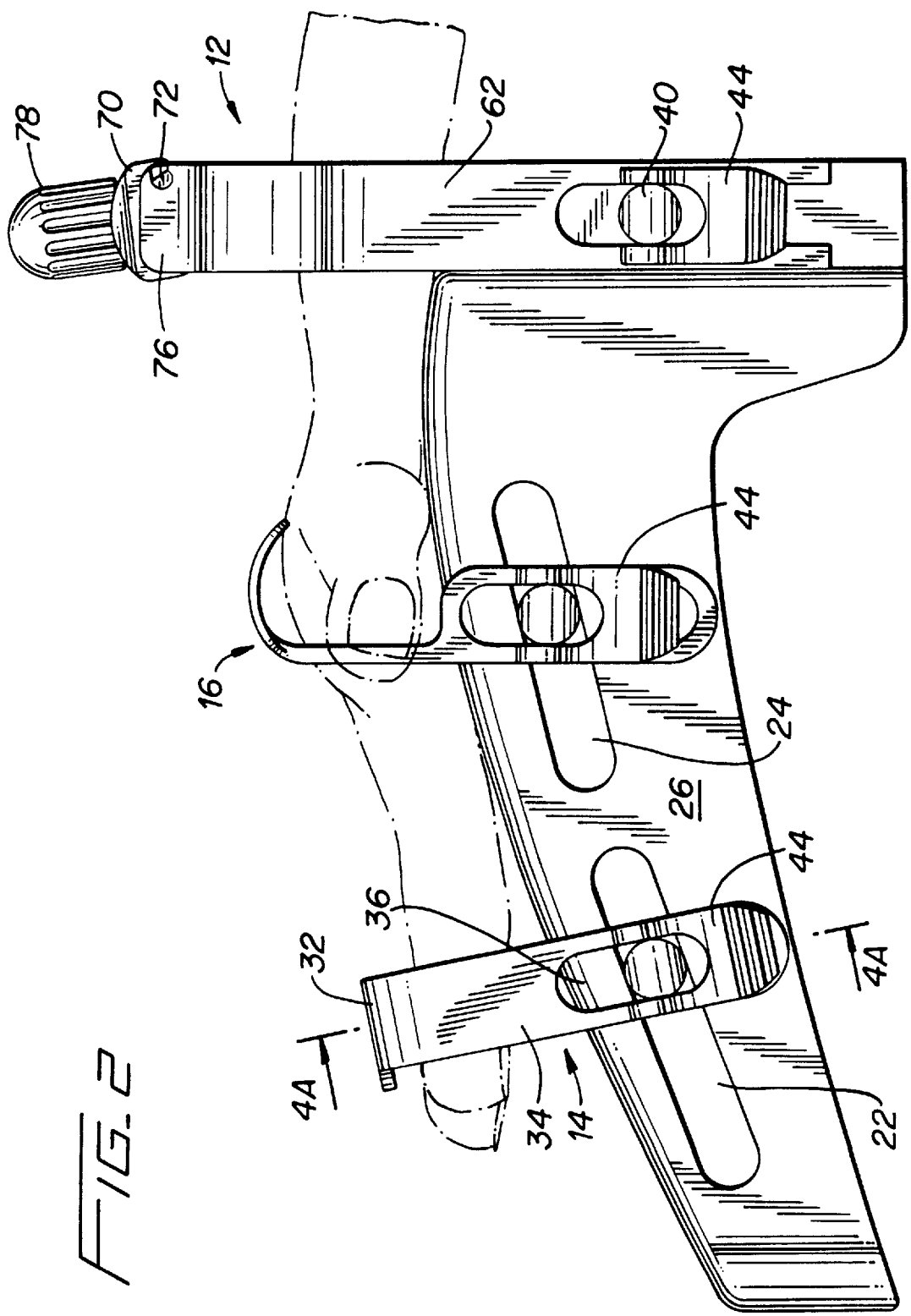

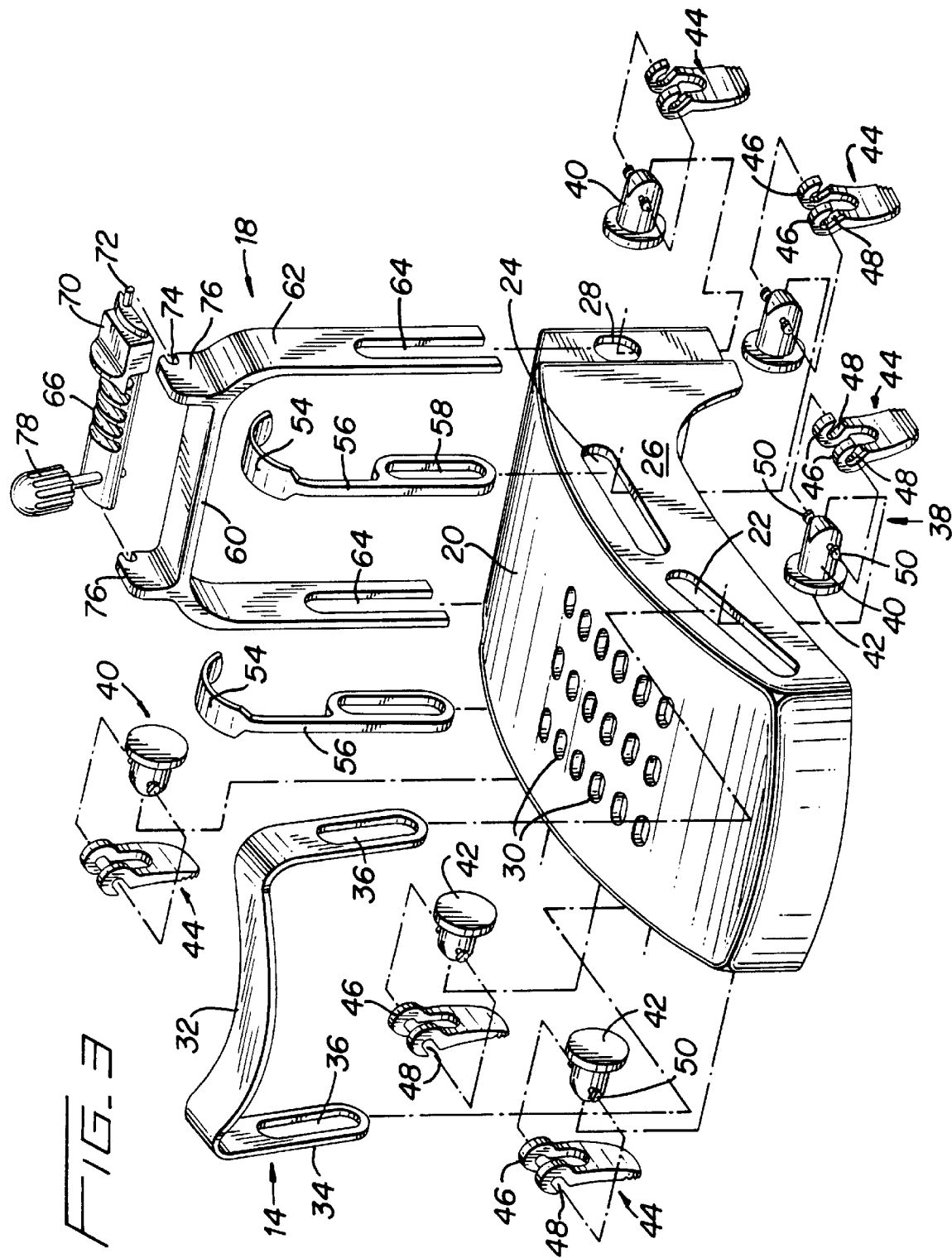

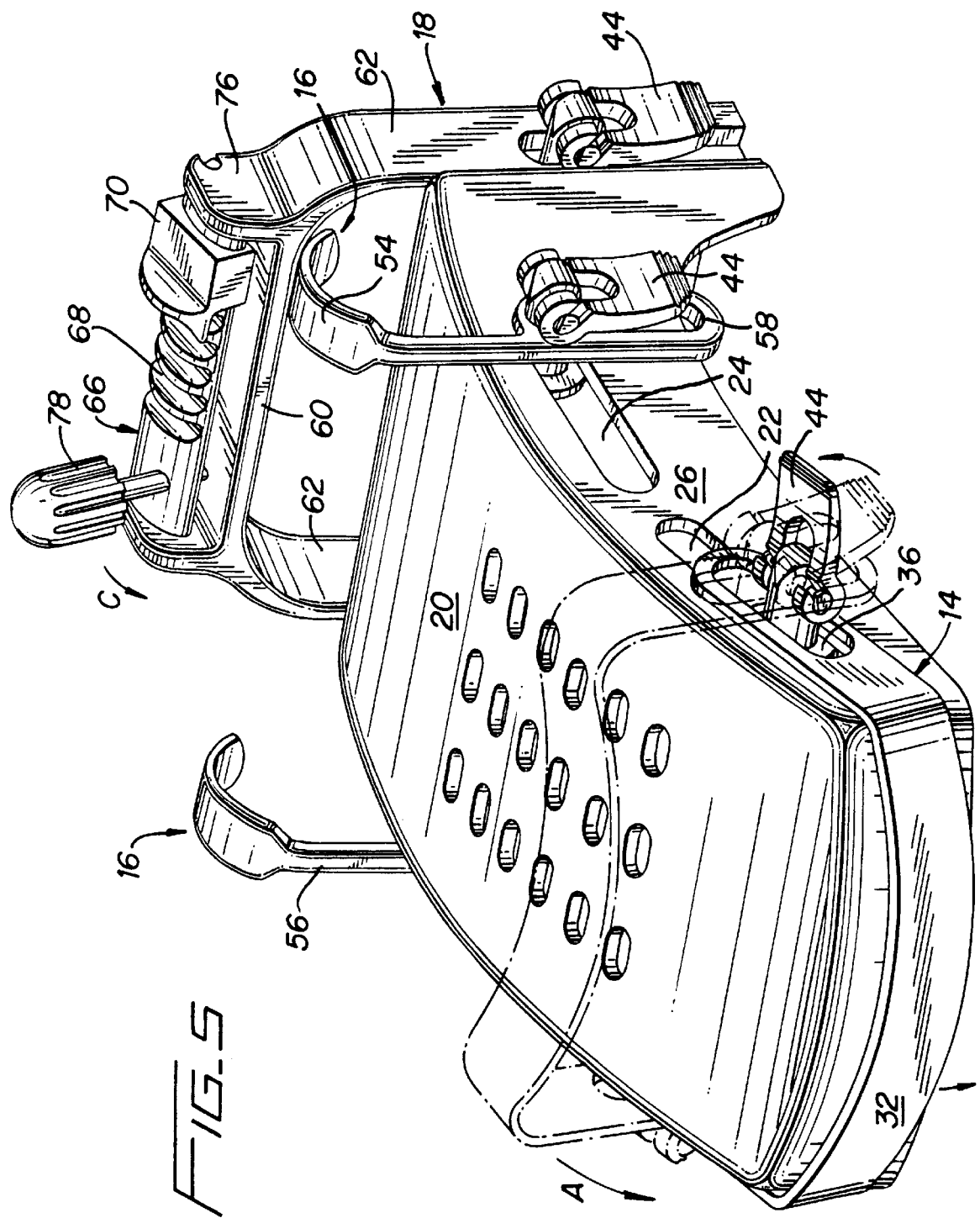

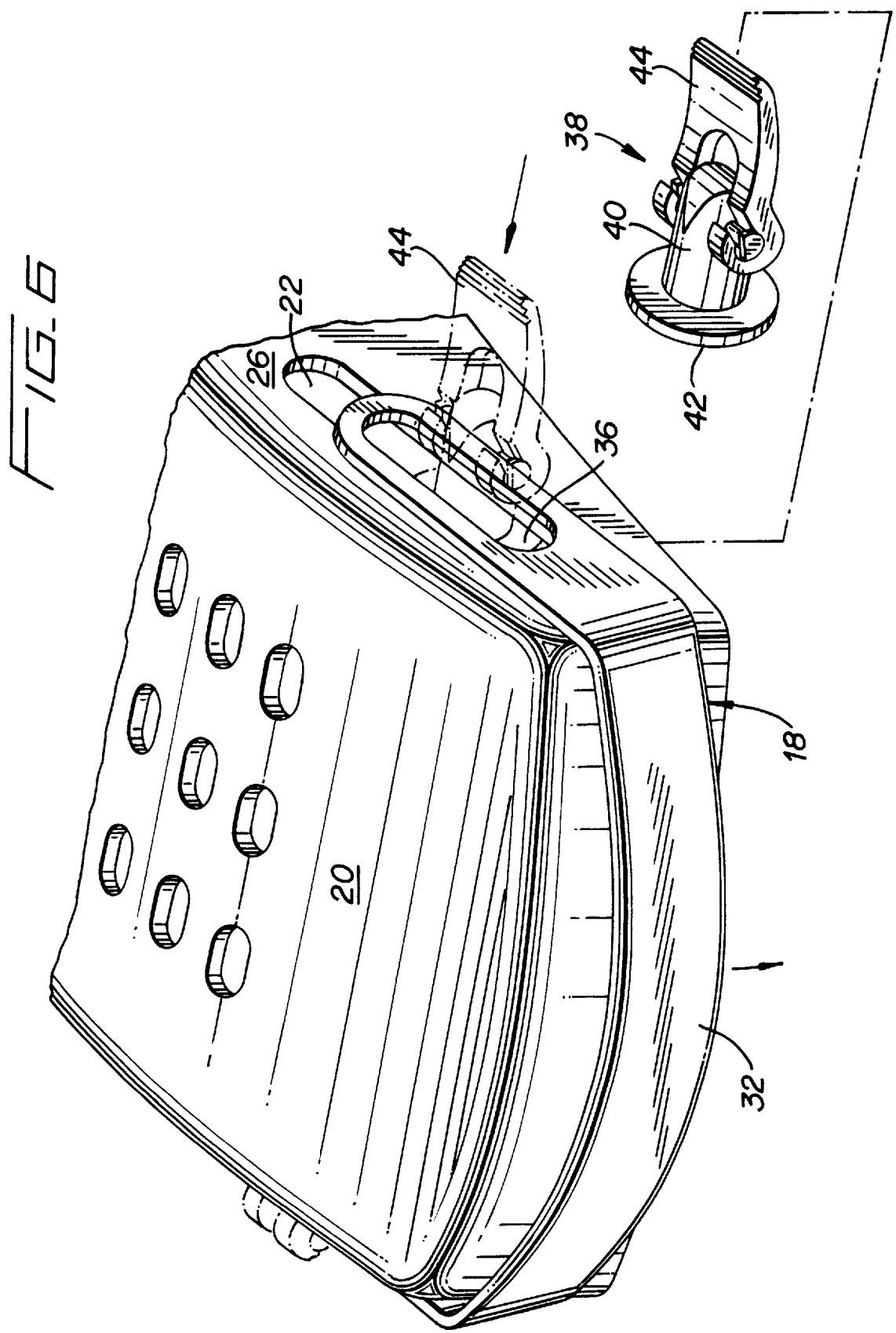

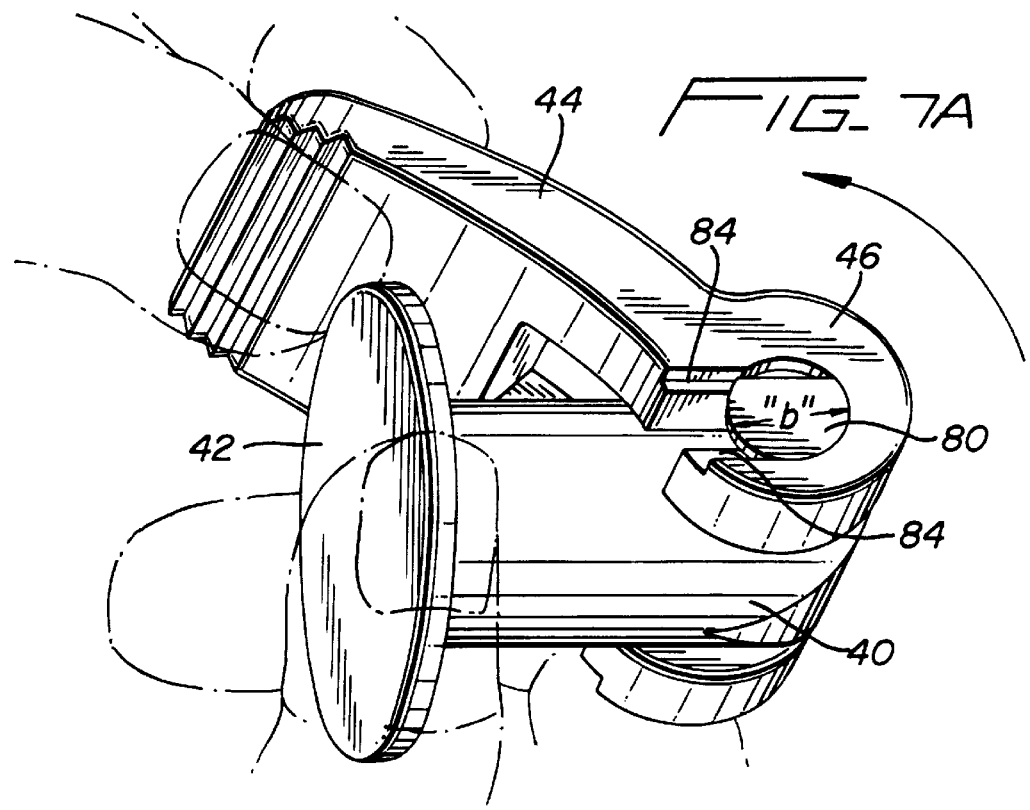
FIG_ 7A
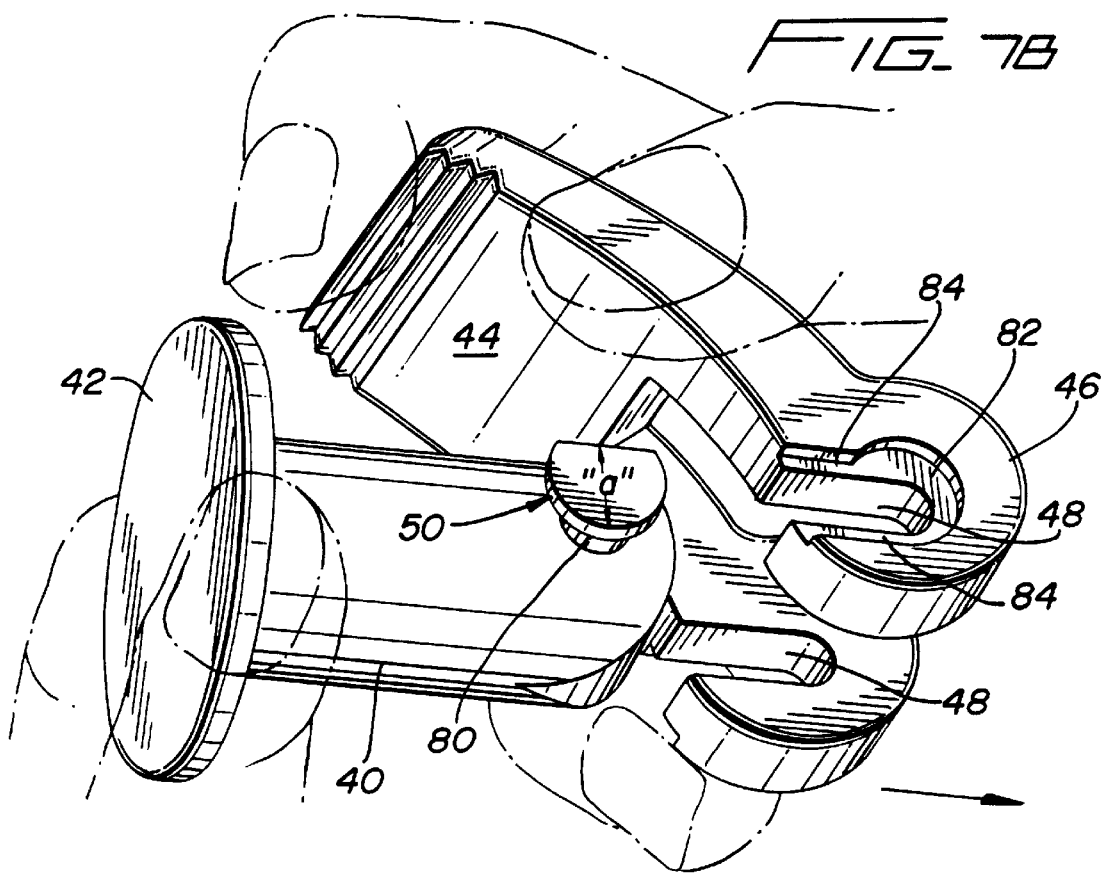
FIG_ 7B

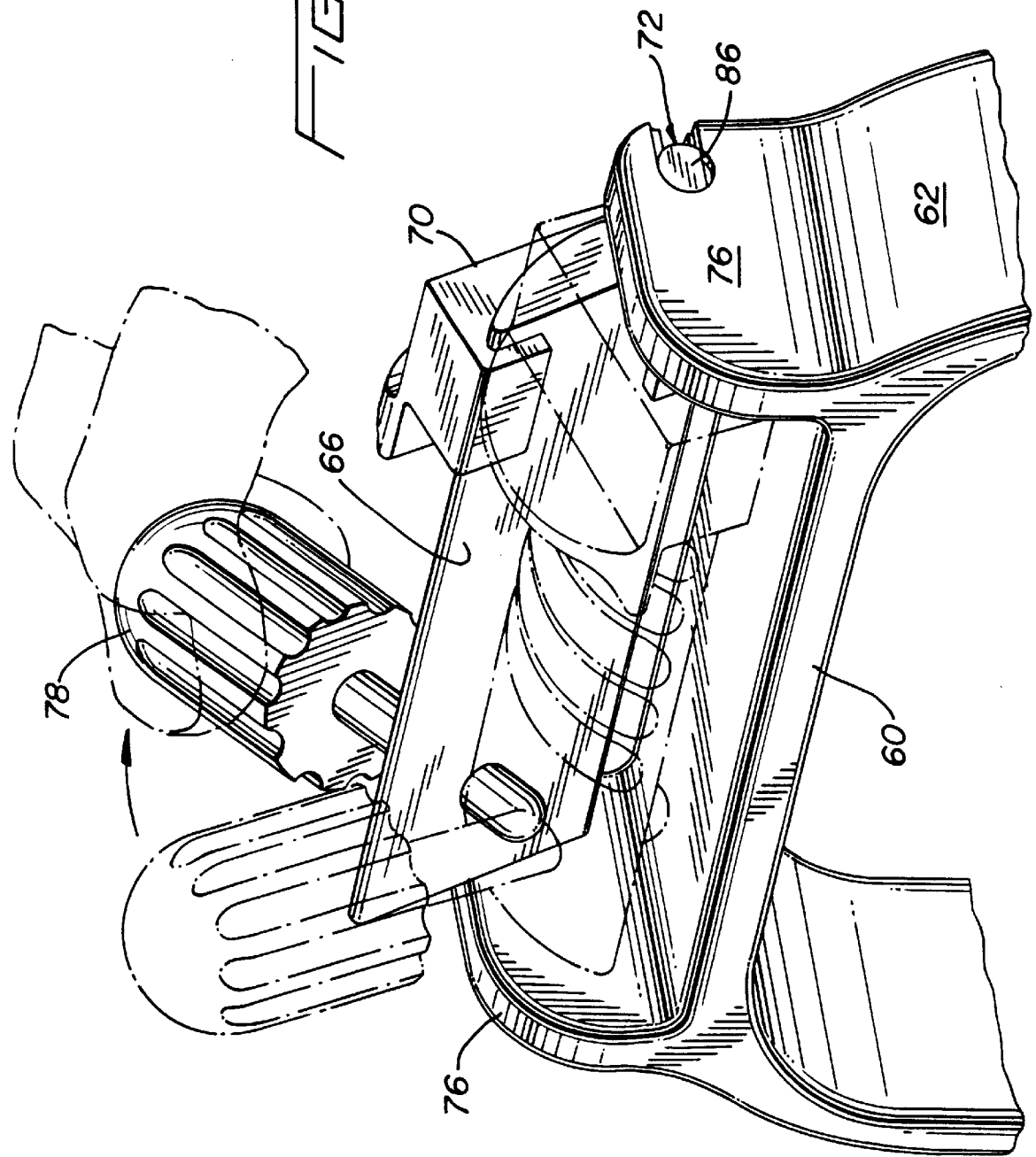

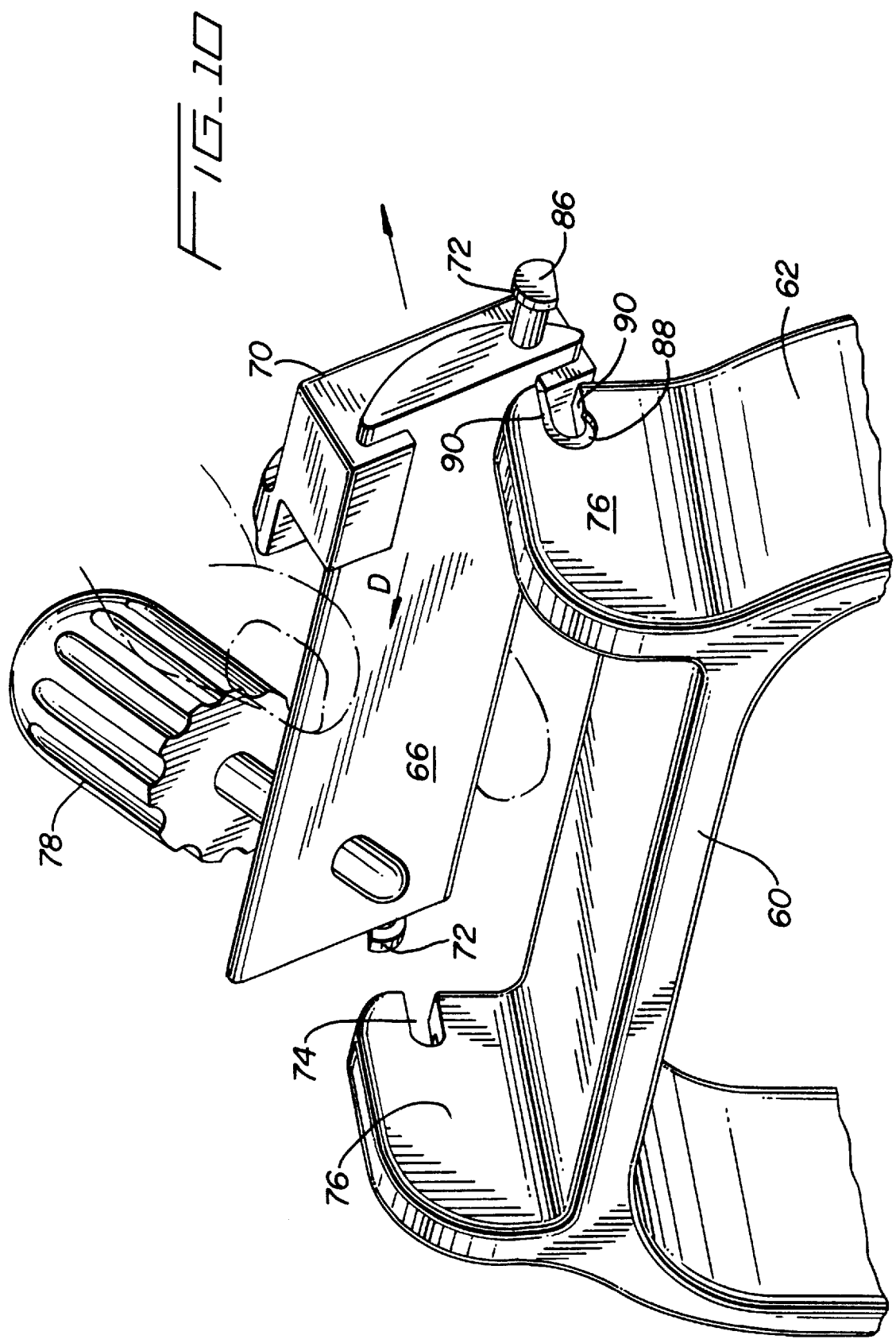

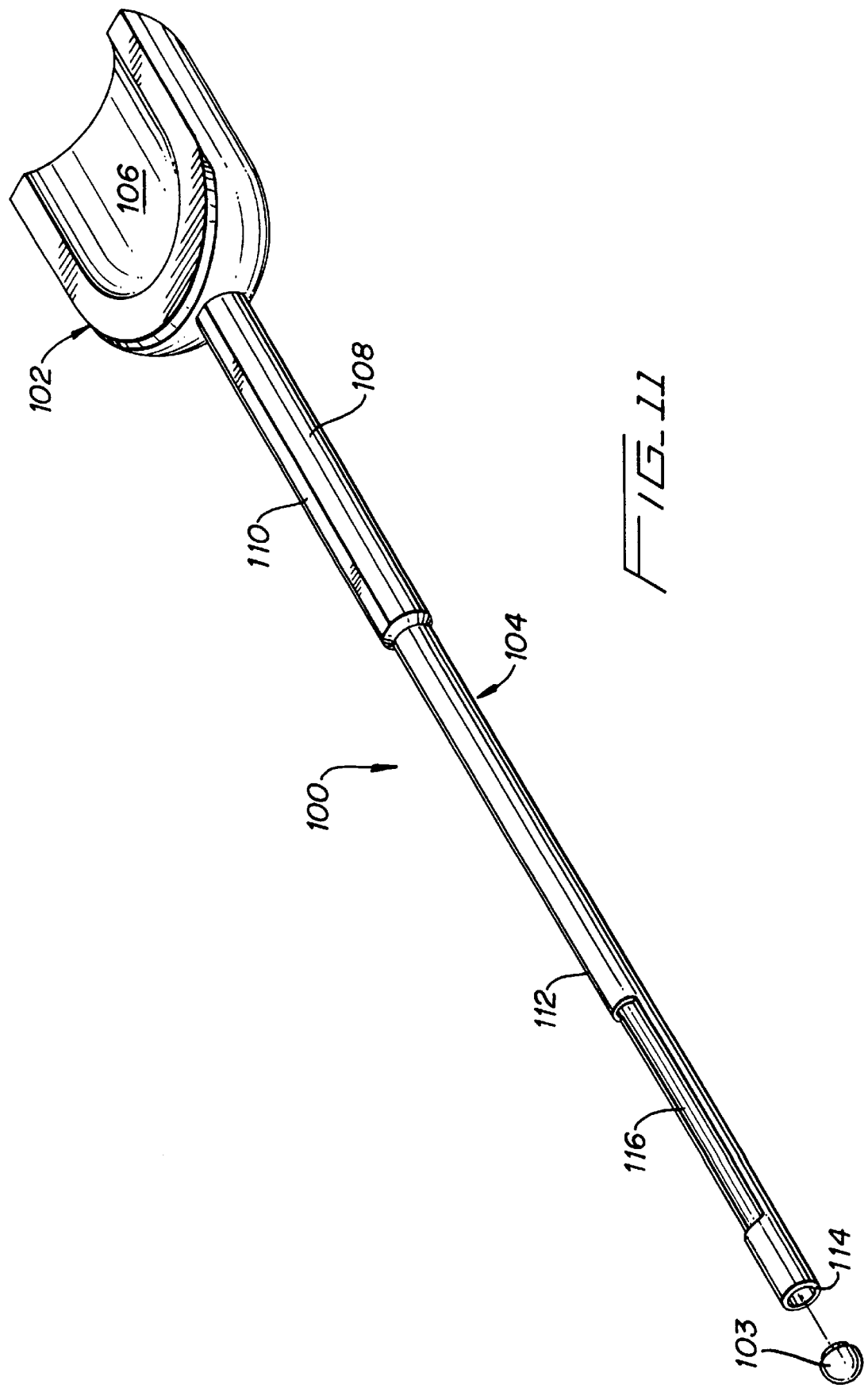

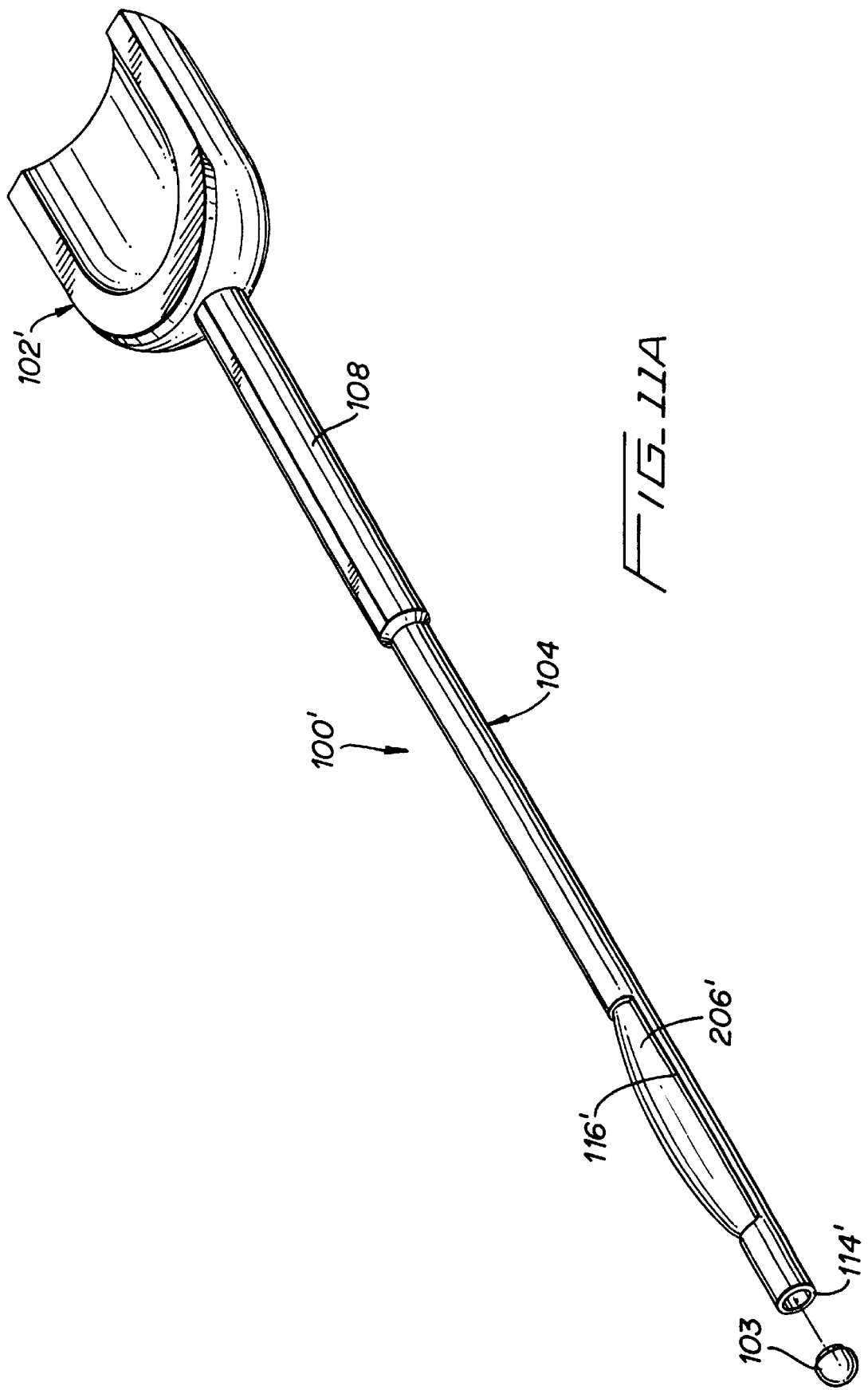

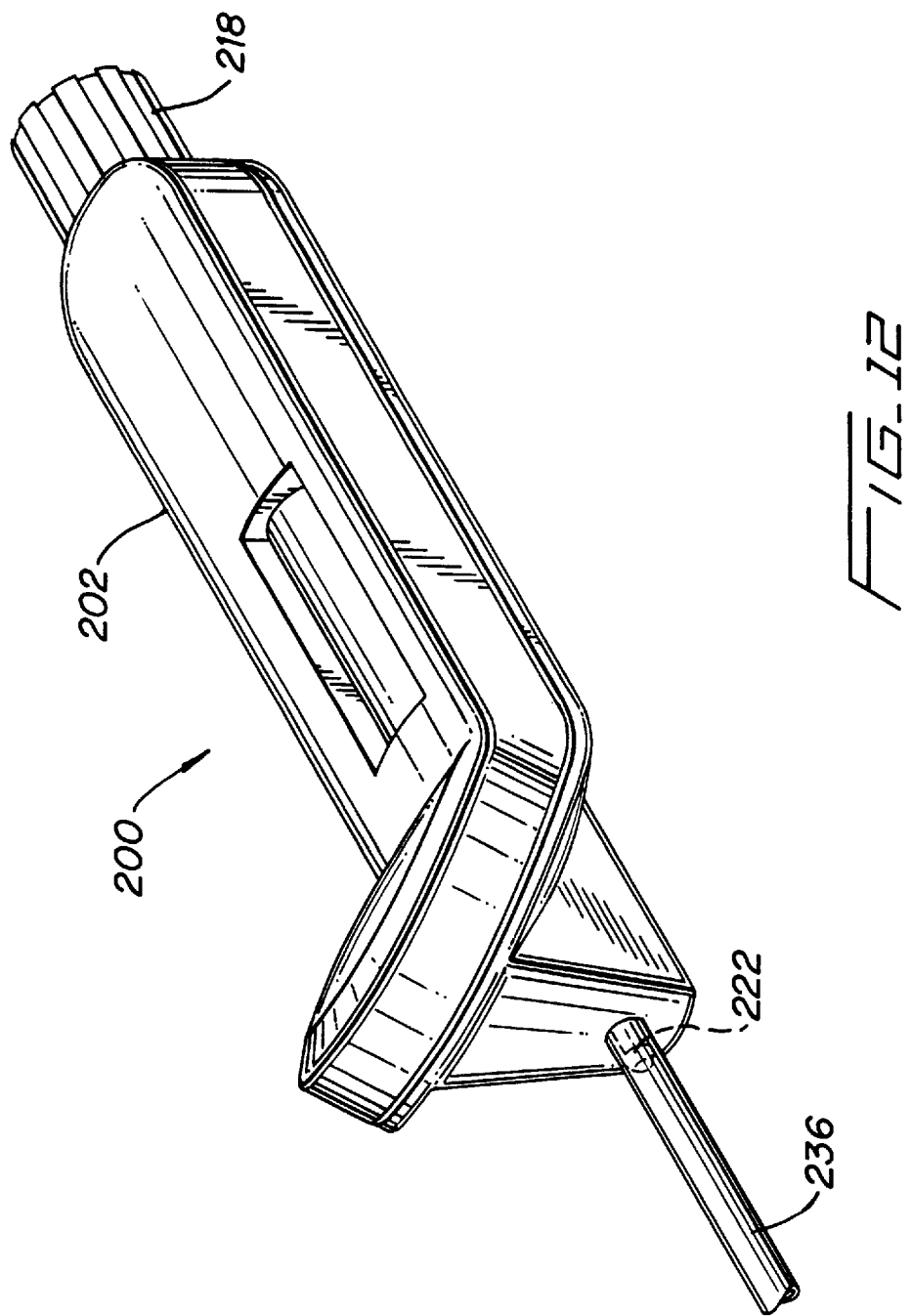

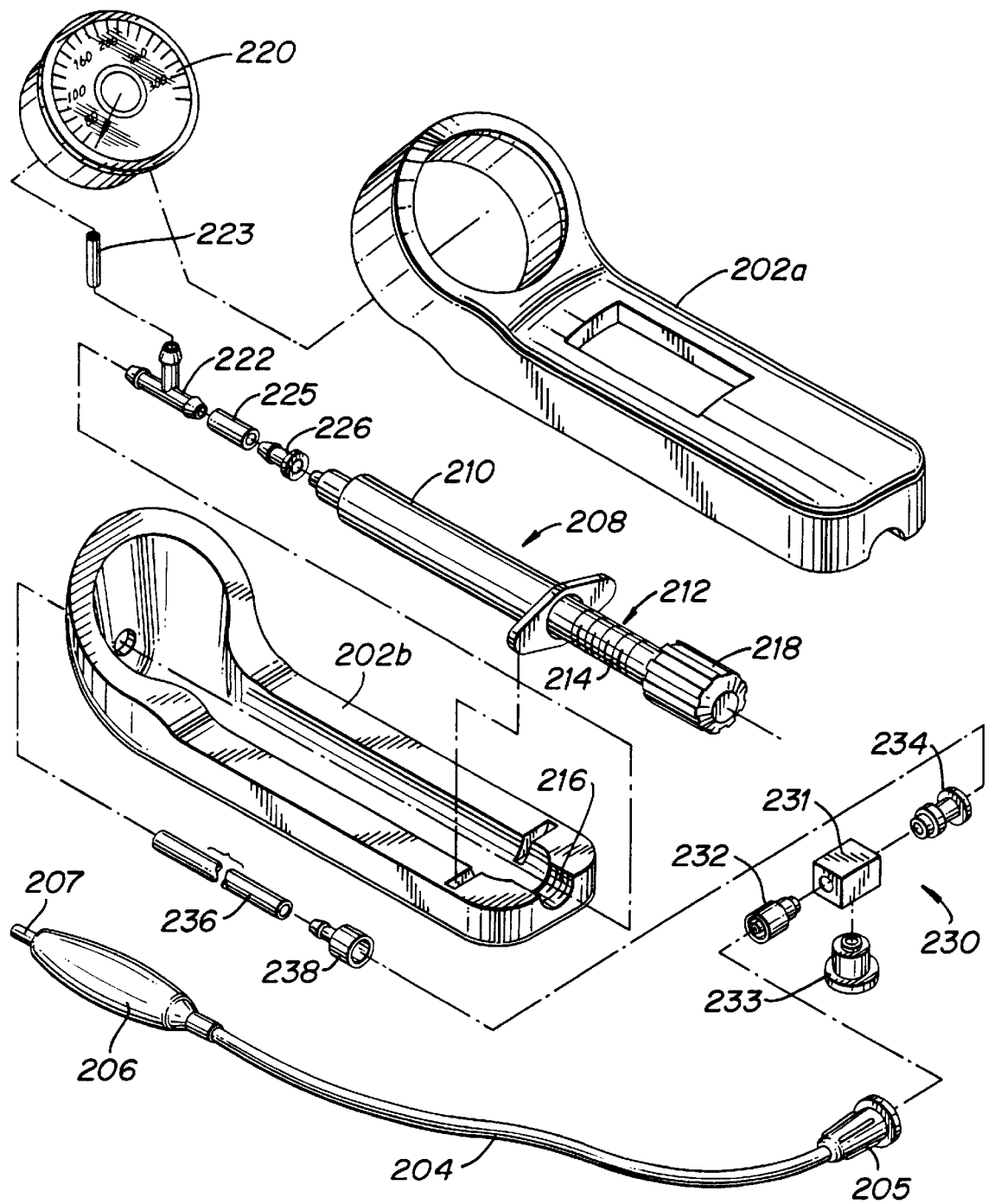
FIG_13

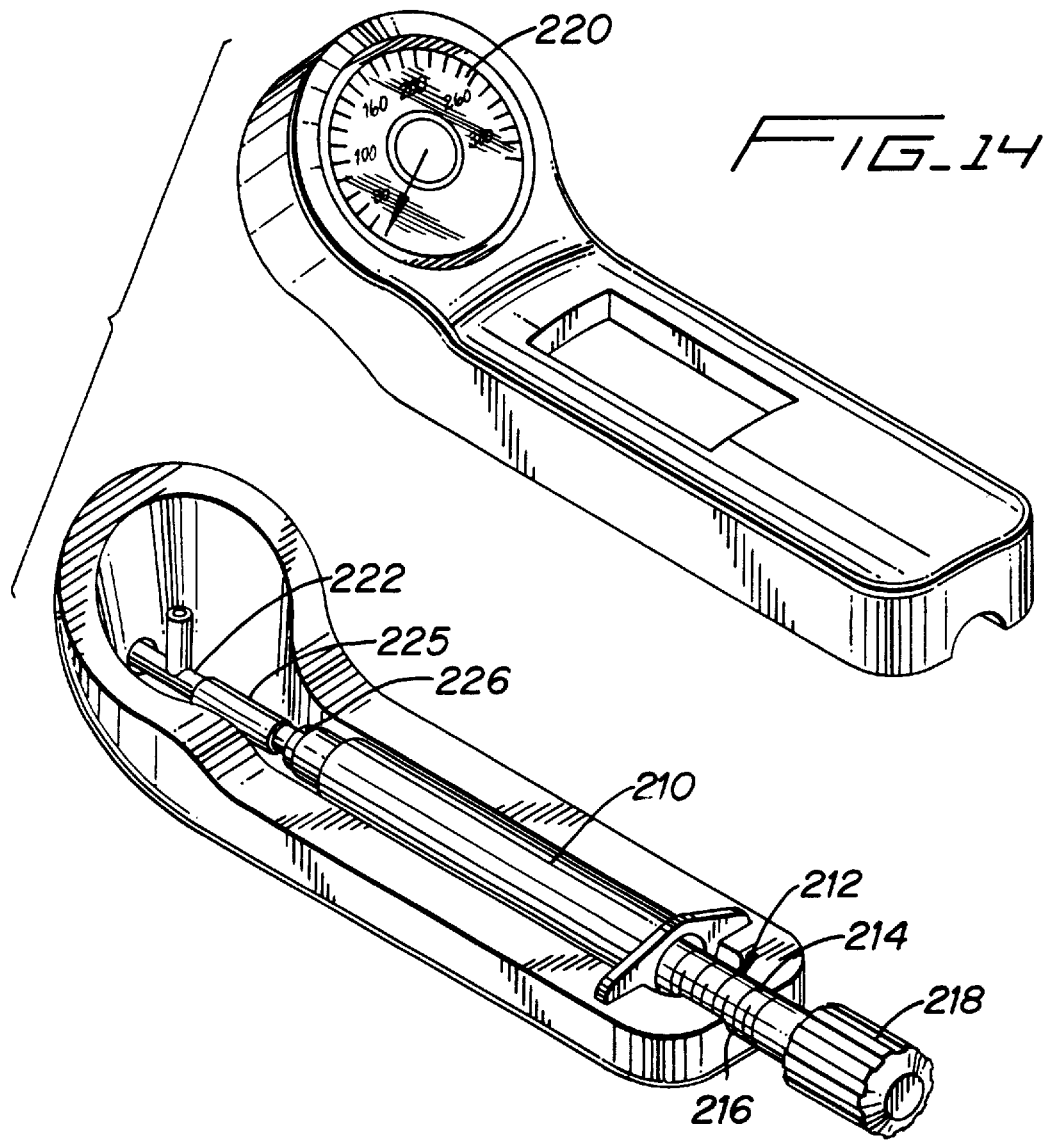
FIG_14
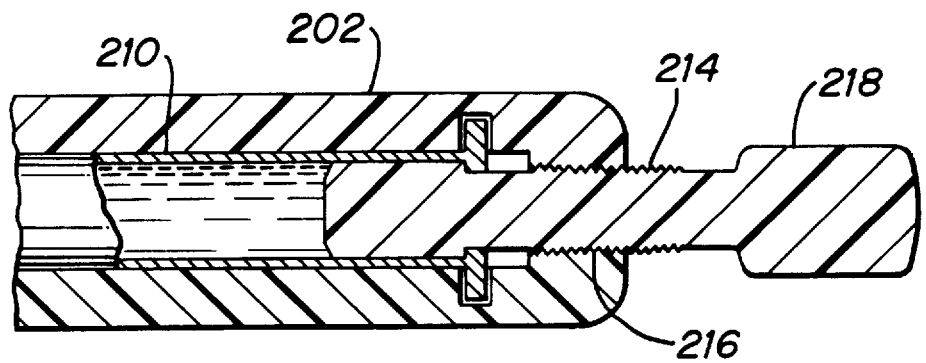
FIG_15

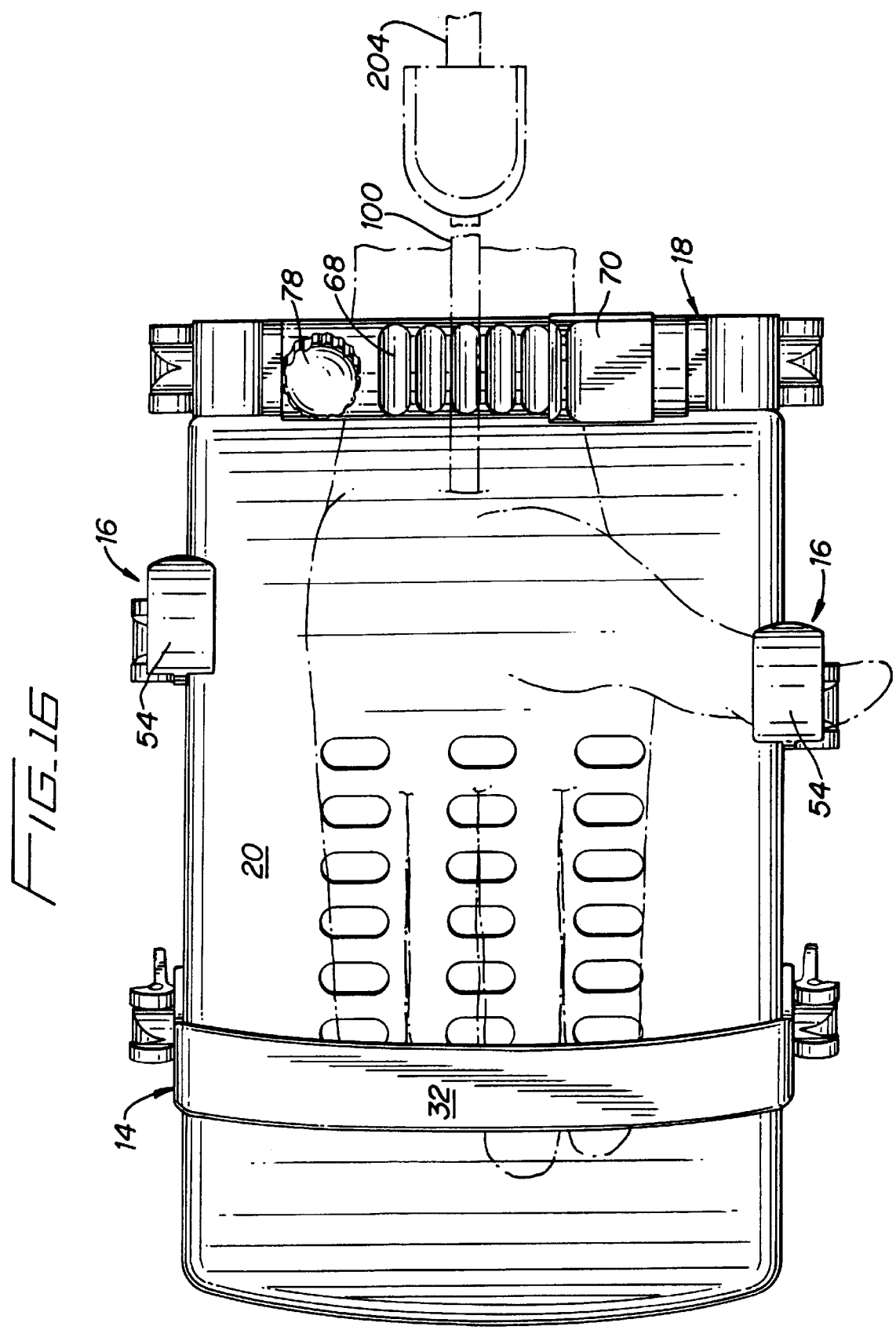

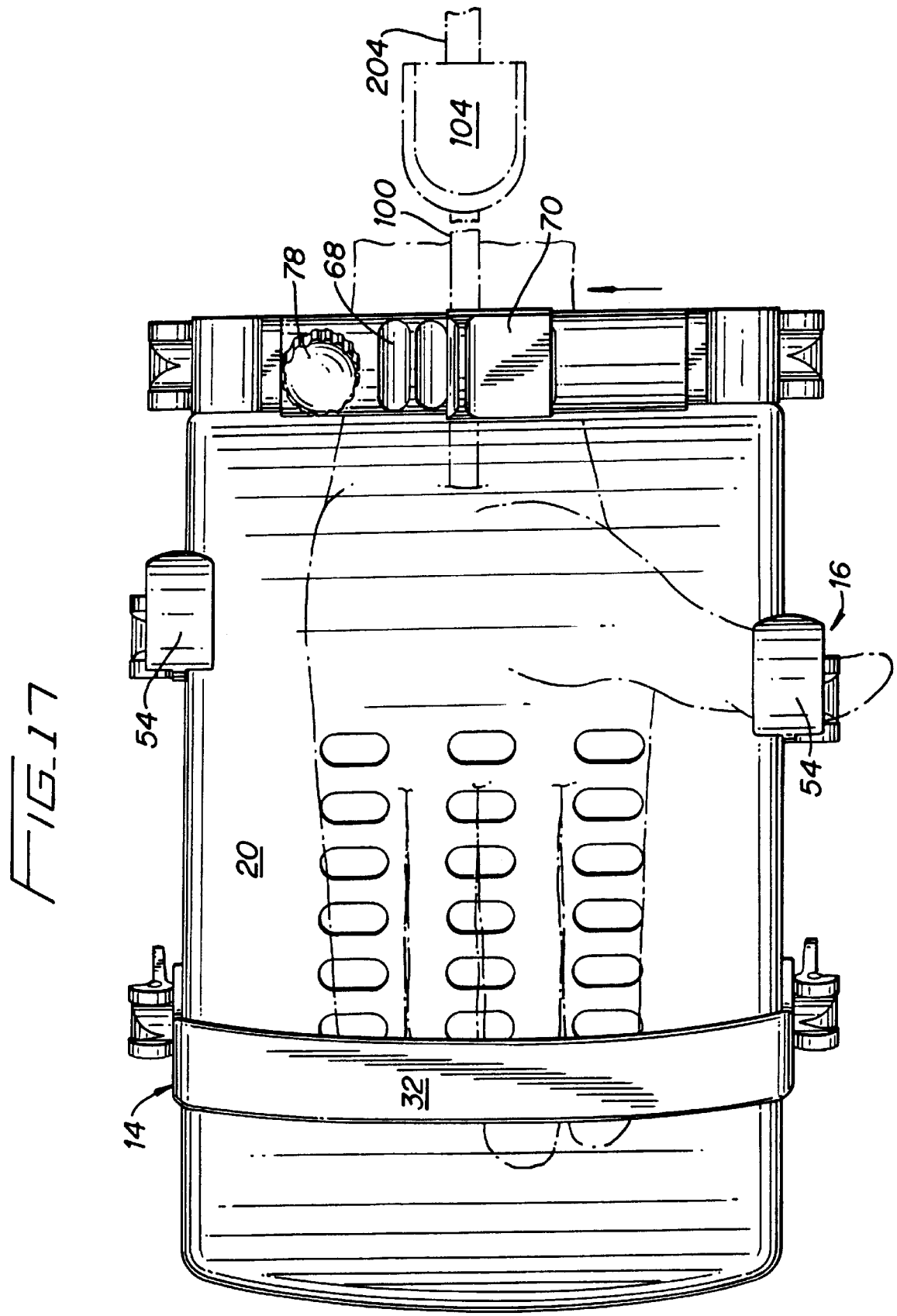

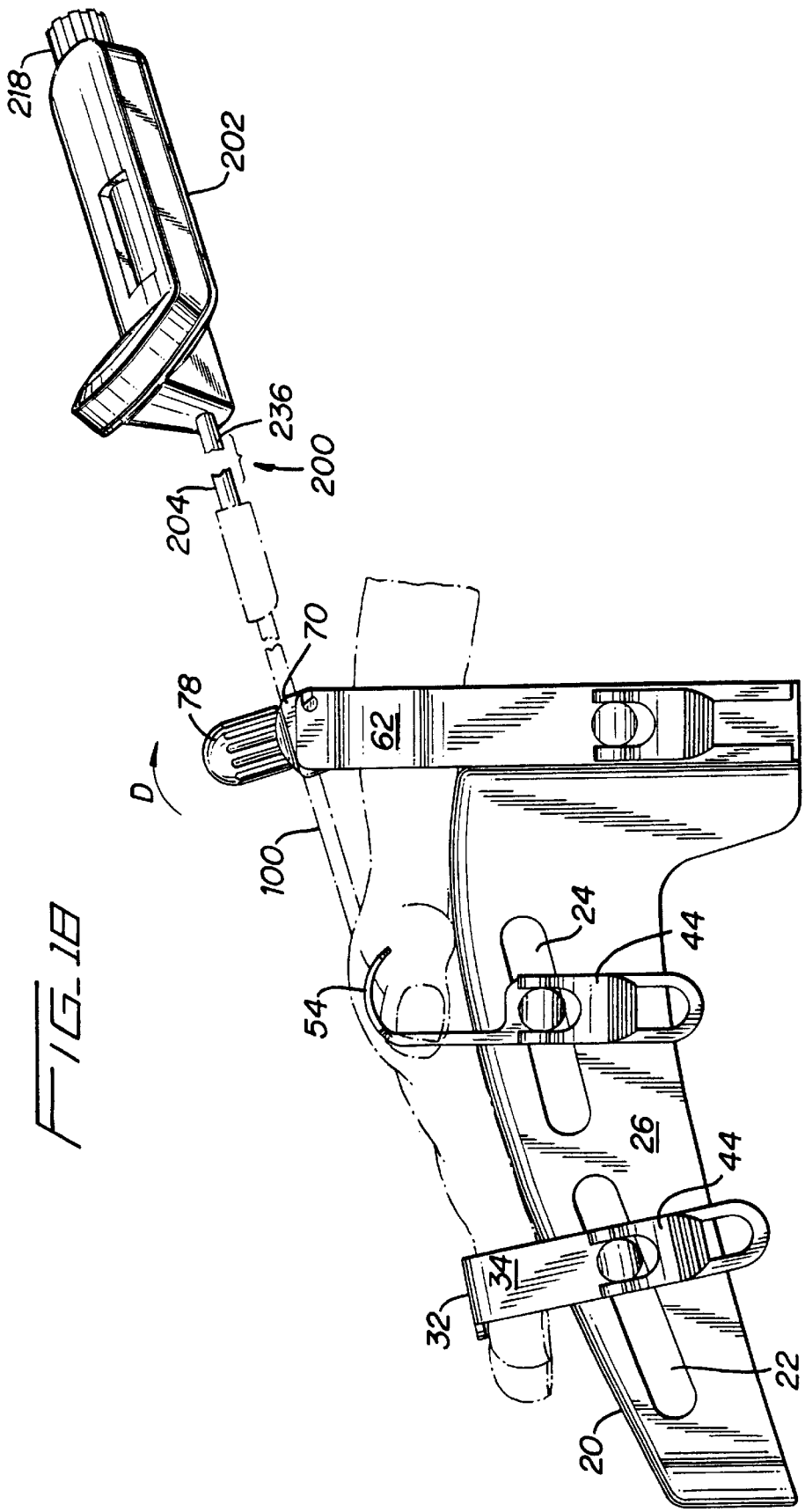

SURGICAL HAND SUPPORT APPARATUS

This is a divisional, of U.S. application Ser. No. 08/319,853 filed Oct. 7, 1994. Now U.S. Pat. No. 5,547,463.

BACKGROUND

1. Technical Field

The present disclosure relates to an apparatus for supporting and immobilizing a patient's hand and wrist during surgery, and, more particularly, relates to a reusable surgical hand support apparatus to be used in conjunction with surgical procedures involving the treatment of carpal tunnel syndrome.

2. Background of Related Art

Surgical procedures involving a person's hand require the hand to be fully supported and immobilized during the surgical procedure and, preferably, retained in a prostrate manner permitting full access for the introduction of surgical instrumentation within the targeted area. This is particularly significant in procedures involving the treatment of carpal tunnel syndrome, where access to the carpal tunnel ligament must be unimpeded to permit insertion of surgical instrumentation within the carpal tunnel defined by the ligament.

Surgical hand support devices are well known in the art. For example, U.S. Pat. No. 5,140,998 to Vickers describes a surgical hand restrainer including a plate for supporting the hand, a clamping member for restraining the fingers and a restraining device for retaining the thumb on the support plate. The clamping member is biased to a closed position by a spring. Other restraint devices for supporting a patient's hand are disclosed in U.S. Pat. Nos. 4,982,744 (an immobilizing apparatus including a composite sheet having an adhesive surface and an arm board) and 4,941,480 (splint for immobilizing a patients arm). U.S. Pat. Nos. 5,025,801, 4,909,264, 3,762,401 and 2,266,230 teach various other devices for temporarily restraining or supporting the hand and/or lower forearm area of the patient.

Certain disadvantages with known surgical hand restraint devices such as those taught in the aforementioned patents are apparent. One disadvantage concerns the relative complexity of the devices, which, consequently, limits accessibility to the patient's hand and increases the difficulty of sterilizing the device after each use. Sterilization of surgical instrumentation has become of extreme significance in recent years due to the increased presence of transmittable diseases such as AIDS, hepatitis, etc. . . The particular structures of known hand support devices do not lend themselves well to sterilization due to the complex arrangement of their component parts which are often inaccessible to sterilization fluids or gases. Consequently, these devices must be either disposed after each use or disassembled and then sterilized. However, due to their structural complexity, disassembly and consequent reassembly of known devices is a tedious and time consuming task. Additionally, certain components of the device may not be adequately sterilized due to their inaccessibility.

U.S. patent application Ser. Nos. 954,383 filed Sep. 16, 1992 and application Ser. No. 08/101,708 filed Aug. 4, 1993 to Berger teach a surgical hand support apparatus particularly contemplated to be used in the treatment of carpal tunnel syndrome. The Berger apparatus includes a base block, a finger support bar which is adjustable toward and away from the base block, a thumb lock assembly having a thumb containment hook and a wrist holding assembly for engaging the patient's wrist. Although the Berger apparatus is well suited for its intended purpose, the present disclosure is directed to further advancements to more effectively assist the surgeon in surgery of the hand, particularly, surgery involving the carpal tunnel ligament. The apparatus of the present disclosure is relatively simple in construction. Further, the present apparatus can be readily disassembled such that each component part may be thoroughly sterilized and subsequently reassembled with relative ease for subsequent use.

SUMMARY

Generally stated, the present disclosure is directed to a surgical hand support apparatus to support a patient's hand and wrist during surgery, particularly surgery contemplated to relieve the symptoms of carpal tunnel syndrome. The apparatus includes a support member defining a supporting surface on which the patient's hand and wrist are supported. A finger securing mechanism including a finger restraining member is mounted to the support member. The finger restraining member is movable relative to the supporting surface to be positioned to engage the fingers of the patient. A thumb restraining mechanism may also be mounted to the supporting surface. The thumb restraining mechanism includes a thumb restraining member also movable relative to the supporting surface to be positioned to engage the thumb of the patient. In a preferred embodiment, the finger restraining member and the thumb restraining member are each movable in both a general longitudinal and a general vertical direction to thereby accommodate hands of various sizes. The apparatus may also include a wrist securing mechanism having a wrist restraining member. The wrist restraining member is movable in a general vertical direction to engage and retain the patient's wrist against the supporting surface.

At least one quick release mechanism is associated with the finger restraining member, thumb restraining member and wrist restraining member to selectively lock each of the these components at a predetermined position relative to the supporting surface. The preferred quick release mechanism includes a locking latch which is movable between an engaged position wherein the respective restraining member is locked at the predetermined position and a disengaged position wherein the respective restraining member is capable of moving relative to the supporting surface. Preferably, the finger and wrist restraining member has two quick release mechanisms, one on each side of the respective member.

The apparatus further includes an instrument support member mounted to the wrist restraining mechanism. The instrument support member incorporates supporting means for supporting a surgical instrument used in surgery in a fixed position relative to the supporting surface of the support member. The preferred supporting means includes at least one groove formed in an upper surface of the instrument support member and dimensioned to accommodate the surgical instrument. The angular orientation of the instrument support member may be adjustable, thereby providing the capability of adjusting the angular orientation of the surgical instrument supported thereby. A set screw, may be provided to limit movement of the instrument support member in one direction and to pivot the support member in another direction.

A method of use of the surgical hand support apparatus with a guiding instrument and a balloon catheter for carpal tunnel surgery is also disclosed.

BRIEF DESCRIPTION OF THE DRAWINGS

Preferred embodiments of the disclosure are described hereinbelow with reference to the drawings wherein:

FIG. 1 is a perspective view of a surgical hand support apparatus constructed in accordance with the principles of the present disclosure;

FIG. 2 is a side plan view of the apparatus of FIG. 1 with a patient's hand shown supported by the apparatus;

FIG. 3 is an exploded perspective view of the apparatus of FIG. 1;

FIG. 5 is a perspective view of the apparatus of FIG. 1 illustrating movement of the release mechanism for disassembling the apparatus;

FIG. 6 is an enlarged perspective view of the finger restraining member illustrating the method for its disassembly;

FIGS. 7A–7B are enlarged perspective views of the quick release mechanism illustrating the method for its disassembly;

FIG. 9 is an enlarged perspective view of the wrist restraining member illustrating the method for disassembling the instrument support member from the wrist restraining member;

FIG. 10 is a view similar to FIG. 9 illustrating the instrument support member removed from the wrist restraining member;

FIG. 11 is an enlarged perspective view of a surgical guiding instrument to be used in conjunction with the apparatus of FIG. 1;

FIG. 11A illustrates a perspective view of an alternate embodiment of a surgical guiding instrument;

FIG. 12 is a perspective view of a catheter housing.

FIG. 13 is an exploded perspective view of the catheter housing, connectors and tubing;

FIG. 14 is a perspective view of the catheter housing with the housing half sections separated to illustrate the syringe assembly positioned therein;

FIG. 15 is a side cross-sectional view of the catheter housing;

FIG. 16 is a top plan view of the apparatus of FIG. 1 illustrating the surgical guiding instrument of FIG. 11 supported by the instrument support member of the apparatus and positioned within the patient's hand;

FIG. 17 is a view similar to the view of FIG. 16 illustrating the guiding instrument of FIG. 11 securely retained within the instrument support member by a slidable locking member;

FIG. 18 is a side plan view illustrating the catheter positioned within the patient's hand in accordance with a preferred method for treating carpal tunnel syndrome.

DETAILED DESCRIPTION OF THE PREFERRED EMBODIMENT

Figure 3A:
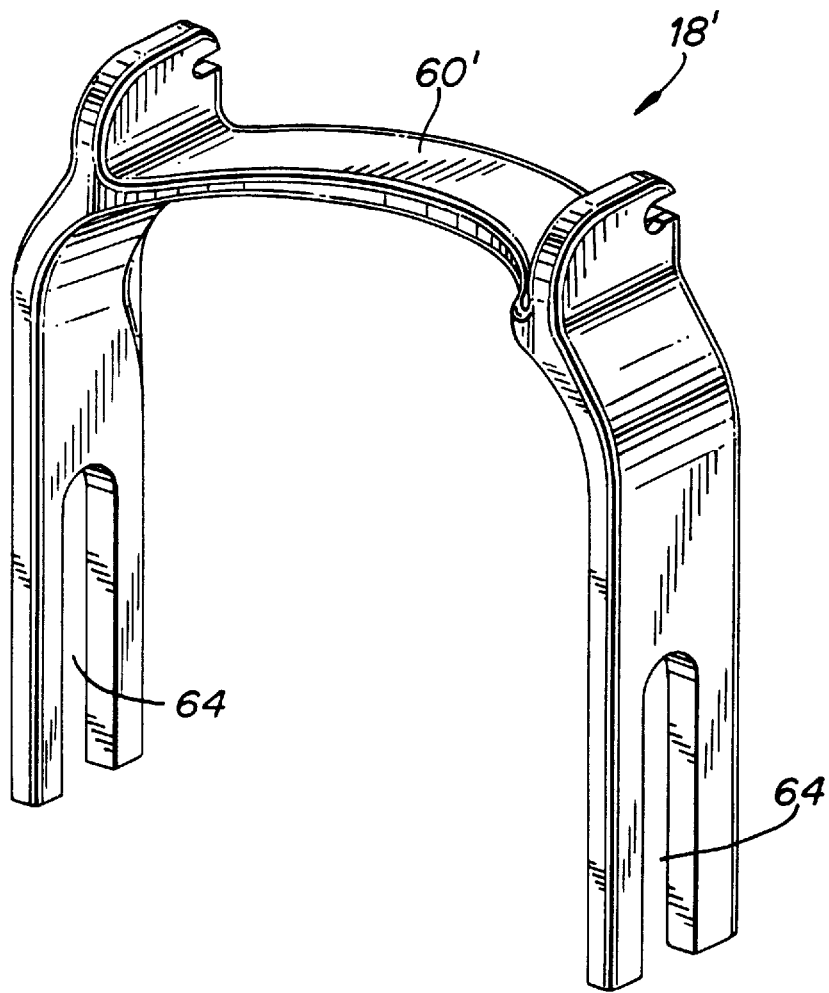
FIG. 3A is a perspective view of an alternate embodiment of the wrist retraining member.

Referring now to the drawings in detail in which like reference numerals identify similar or identical elements throughout the several views, FIG. 1 illustrates in perspective view the surgical hand support apparatus in accordance with the principles of the present disclosure.

Apparatus 10 is intended to support and restrain the patient's hand and wrist in a fixed position during surgery. Apparatus 10 is particularly contemplated for use during surgery to relieve the symptoms of carpal tunnel syndrome although it is to be appreciated that the apparatus has application in other types of surgical procedures to support the hand such as vascular repair, nerve repair and re-attachment of digits. As will be appreciated from the description provided below, apparatus 10 is capable of being fully disassembled, i.e., the apparatus may be taken apart to its basic components. This feature facilitates sterilization of the components so that the apparatus 10 can be re-used.

Referring now to FIGS. 1–3, apparatus 10 includes support member 12, finger restraining member 14, thumb restraining member 16 and wrist restraining member 18. Support member 12 is advantageously dimensioned to support the patient's hand and wrist in a prostrate position, e.g., with the palm of the patient facing upwardly. Support member 12 has a slightly arcuate upper surface 20 upon which the patient's hand and wrist are positioned. The curved configuration of upper surface 20 accommodates for the natural curvature defined at the juncture of the patient's wrist and hand to fully support these bodily components as best shown in FIG. 2.

Support member 12 includes first and second pairs of apertures 22, 24 extending longitudinally in opposed side walls 26 of the support member and a third pair of apertures 28. Apertures 22, 24 serve to mount finger restraining member 14 and thumb restraining member 16, respectively, as will be appreciated from the description provided below. Similarly, apertures 28 serve to mount wrist restraining member 18. A plurality of openings 30 may be provided in upper surface 20, preferably parallel thereto, to enable the insertion of pegs or rods to keep selected fingers spread apart during the surgical procedure.

Referring still to FIGS. 1–3, finger restraining member 14 includes a cross bar 32 which traverses upper surface 20 of support member 12 and first and second leg portions 34 extending downwardly from the cross bar 32. Leg portions 34 each include an elongated aperture 36 extending along its length. The cross bar 32, as shown, curves toward the front of support member 12 to accommodate different finger lengths. A quick release mechanism, generally identified as reference numeral 38, is provided to releasably lock finger restraining member 14 at desired longitudinal and vertical locations relative to support member 12. Quick release mechanism 38 consists of locking stud 40 having circumferential flange 42 at one end and a locking latch 44 pivotally mounted to the locking stud 40 at its other end. In the preferred embodiment, locking latch 44 includes two spaced bifurcations 46. Each bifurcation 46 has a slot 48 formed therein which accommodates a pivot pin 50 extending transversely from locking stud 40 to pivotally mount the locking latch 44 to the locking stud 40. The particular features of pivot pins 50 will be discussed in greater detail below. In the mounted position of quick release mechanism 38, locking stud 40 extends through apertures 22, formed in side walls 26 of support member 12 and through apertures 36 of leg portions 34 of finger restraining member 14, with circumferential flange 42 abutting against the interior portion of side wall 26 and locking latch 44 mounted about pivot pins 50.

Figure 4A:
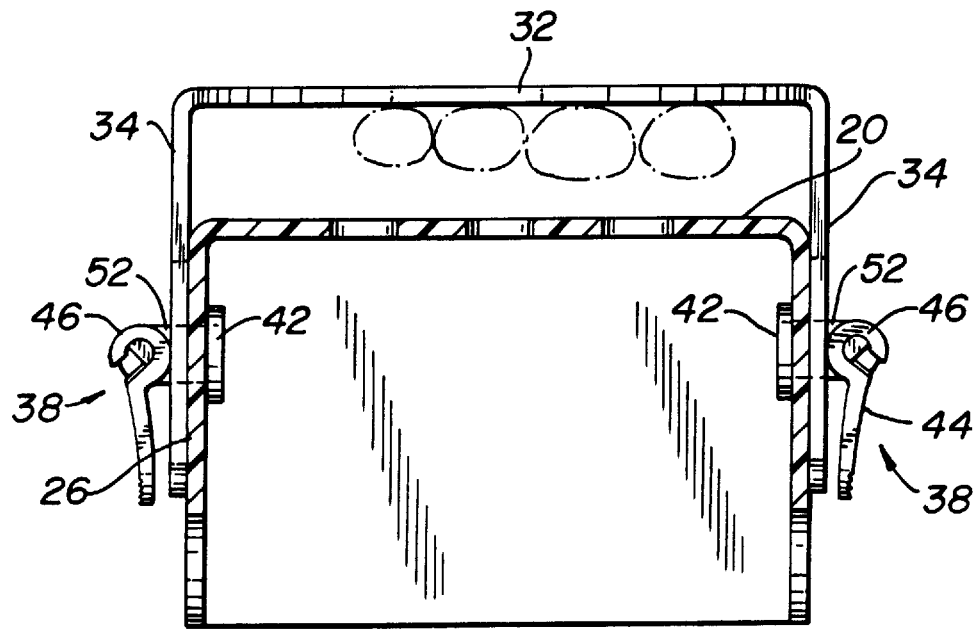
FIG. 4A is a cross-sectional view taken along the lines 4A—4A of FIG. 2 illustrating the finger restraining member in position to engage the fingers of the patient.

Quick release mechanism 38 is readily movable between a secured position where finger restraining member 14 is securely fixed at a desired position relative to upper surface 20 and a release position where the positioning of finger restraining member 14, both horizontal and vertical, may be selectively adjusted. FIG. 4A depicts the secured position of quick release mechanism 38. In such position, locking latch 44 is positioned downwardly whereby the outer arcuate portions 52 of each spaced bifurcation 46 frictionally engages the leg portions 34 of finger restraining member 14.

Figure 4B:
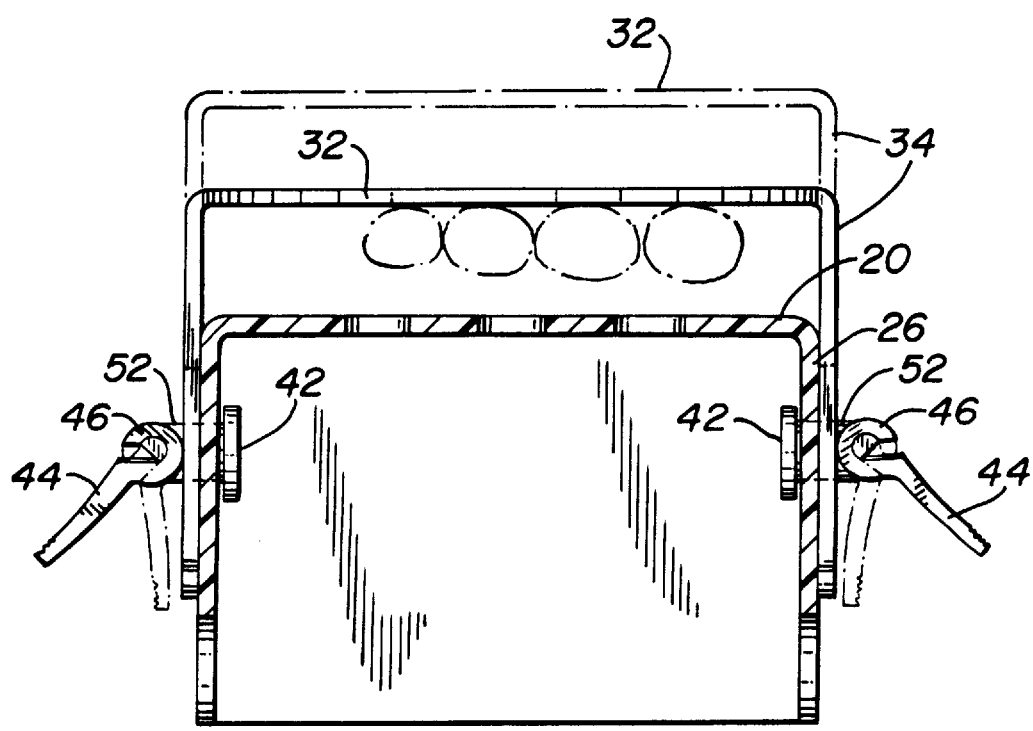
FIG. 4B is a view similar to the view of FIG. 4A illustrating the range of vertical movement of the finger restraining member.

In the release position of quick release mechanism 38, each locking latch 44 is pivoted upwardly as shown in FIG. 4B such that the outer arcuate portion 52 releases from its frictional engagement with leg portions 34 of finger restraining member 14. Consequently, finger restraining member 14 is free to move in a first direction, e.g., longitudinal, and a second direction, vertical. It is to be appreciated that the particular dimensioning of apertures 22 in side walls 26 permit adjustability of finger restraining member 14 in the longitudinal direction while apertures 36 in finger restraining member 14 permit adjustability of the finger restraining member 14 in the vertical direction. FIG. 4B illustrates the range of vertical movement of finger restraining member 14.

Referring again to FIGS. 1–3, the pair of thumb restraining members 16 will now be described. In the embodiment shown, two thumb restraining members 16 are provided, one on each side of support member 12 so that the apparatus 10 may accommodate either the left or right hand of the patient. It is also contemplated that in an alternate embodiment, a single thumb restraining member 16 could be provided which could be mounted on either side of the support member 12 to accommodate the right or left hand of the patient. Each thumb restraining member 16 includes an arcuate thumb engaging portion 54 and a leg portion 56 extending downwardly from the thumb engaging portion and having an elongated aperture 58 formed therein. The curved thumb engaging portion 54 engages and immobilizes the patient's thumb when thumb restraining member 16 is in a secured position. Each thumb restraining member 16 includes a quick release mechanism 38 for positively securing the thumb restraining member, which is identical to the quick release mechanism described above in connection with finger restraining member 14. Thus, through the provision of quick release mechanism 38, in conjunction with the aperture 24 formed in side wall 26 and aperture 58 of thumb restraining member 16, the positioning of the thumb restraining member 16 can be selectively adjusted in both a first, e.g., longitudinal, direction and a second, e.g., vertical, direction.

Wrist restraining member 18 includes horizontal wrist engaging portion 60 and two leg portions 62 extending downwardly from the wrist engaging portion 60. Wrist engaging portion 60 engages and immobilizes the patient's wrist when restraining member 18 is in a secured position. Leg portions 62 each possess a channel 64 (FIG. 3) which partially extends along its length to accommodate quick release mechanism 38. Wrist restraining member 18 is selectively movable in a general vertical direction through the provision of channels 64 and can be securely fixed at a desired vertical position by a quick release mechanism 38. Quick release mechanism 38 functions in an identical manner to the quick release mechanism 38 described in connection with finger restraining member 14 and thumb restraining member 16.

In an alternate embodiment of FIG. 3A, wrist restraining member 18' includes wrist engaging portion 60' which is curved in a proximal (rearward) direction to increase the mobility of the guiding instrument discussed below with respect to FIG. 11.

An instrument support member 66 is mounted to wrist restraining member 18. Support member 66 is intended to support a surgical instrument, such as a guiding instrument, catheter, grasping instrument, etc. . . , used during a surgical procedure. An example of an instrument intended to be used with apparatus 10 during carpal tunnel surgery is illustrated in FIG. 11. This instrument will be discussed in greater detail below. Instrument support member 66 includes a plurality (preferably 5) of generally longitudinally extending grooves 68 (FIG. 1) formed in its upper surface which accommodates the instrument. An instrument holder 70 is slidably mounted to the instrument support member 66 and is adapted to move to substantially enclose the instrument received within groove 68 to prevent lateral and vertical movement of the instrument.

As shown in FIGS. 1–3, instrument support member 66 is mounted to wrist restraining member 18 via a pair of pin projections 72 extending outwardly from each side of instrument support member 66 and received within slots 74 formed in upright portions 76 which extend upwardly from wrist engaging portion 60. This particular mounting method permits the angular orientation of instrument support member 66 to be selectively adjusted relative to the support member 20 (i.e., the instrument support member is capable of pivoting about its mounting projections 72). Consequently, the orientation of the surgical instrument supported by instrument support member 66 is also adjustable, the significance of which will be described hereinbelow. Preferably, pin projections 72 are disposed toward the rear end portion of instrument support member 66 whereby the forward end portion naturally drops downwardly toward support member 12. An adjusting screw 78 extends through instrument support member 66 to contact wrist engaging portion 60 of the wrist restraining member 18. Adjusting screw 78 is rotatable to press firmly against wrist engaging portion 60, thus preventing pivotal movement of support member 66 downwardly towards support member 16 (in the direction of arrow C in FIG. 5). This is described in more detail below.

Referring now to FIGS. 5–9, disassembly of apparatus 10 will now be discussed. As previously noted, the apparatus of the present disclosure can be readily disassembled to its basic component parts whereby the component parts are sterilized and then reassembled for another use. Disassembly of apparatus 10 is as follows. Each quick release mechanism 38 which secures finger restraining member 14 is moved to its release position by pivoting locking latch 44 upwardly such that the latch 44 is generally transverse to sidewall 26 as shown in FIG. 5. Thereafter, finger restraining member 14 is moved forwardly as shown by the directional arrow A in FIG. 5 to align the apertures 36 of finger restraining member 14 with the apertures 22 in side wall 26 as shown in FIG. 6. (In this aligned position, finger restraining member 14 lies below the bottom portion of the support member 12 which is lifted off the table.) Thereafter, the locking latch 44 on both sides is pushed inwardly through aperture 36 in leg portions 34 and aperture 22 in side wall 26 such that locking stud 40 and locking latch 44 are removed from their engagement with the apparatus as shown in FIG. 6. Thereafter, finger restraining member 14 is removed. Each thumb restraining member 16 is disassembled from support member 20 in a similar manner, i.e., locking latch 44 is pivoted upwardly to a release position, thumb restraining member 16 is rotated forwardly to align aperture 58 of the restraining member with aperture 24 of side wall 26 and the locking latch 44 is pushed through the respective apertures to remove the thumb restraining member 16.

Wrist restraining member 18 is disassembled by moving both quick release mechanisms 38 securing the wrist restraining member 18 to their release positions, sliding restraining member 18 upwardly to remove it from locking stud 40, rotating the locking latches 44 to align with apertures 28 of support member 12 and pushing each locking latch 44 and locking stud 40 inwardly. Clearly, alternatively, the thumb restraining member 16 or wrist restraining member 18 can be disassembled first.

FIGS. 7A–7B illustrate the disassembly of quick release mechanism 38 to its component parts. As stated above, locking latch 44 of quick release mechanism 38 is detachably is connected to locking stud 40 via the reception of mounting pins 50 of the locking stud 40 with slots 48 of the locking latch 44. In addition, as detailed in FIGS. 7A–7B, mounting pins 50 each include a flange portion 80 having a generally semicircular shape. Such semicircular shape of flange 80 defines a dimension "a" which is less than a dimension "b" of the flange 80 where dimension "b" is substantially equal to the diameter of the flange 80 (see also FIGS. 8A–8B). Locking latch 44 includes a circumferential recess 82 on a side surface of each bifurcation 46. Recess 82 is in communication with opposed release groove portions 84. In the mounted condition of locking latch 44 as shown in FIG. 4A, flange portion 80 is retained within circumferential recess 82 by engagement thereof with the portions defining the recess 82. More specifically, locking stud 40 is rotationally oriented such that the flange portion 80 defining dimension "b" engages the portions defining recess 82. To disassemble locking latch 44 from locking stud 40, locking latch 44 is pivoted upwardly approximately 270° to the position shown in FIG. 7A such that dimension "a" of flange portion 80 is in alignment with release groove portions 84. Thereafter, locking latch 44 is removed from locking stud 40 by sliding the latch 44 off mounting pin 50 as shown in FIG. 7B.

It is to be appreciated that locking latch 44 cannot be removed from locking stud 40 while the quick release mechanism 38 is mounted to support member 20 because locking latch 44 cannot be pivoted sufficiently upwardly, i.e. 270°, to the position of FIG. 7A because it will be blocked by support member 20.

Figure 8A:
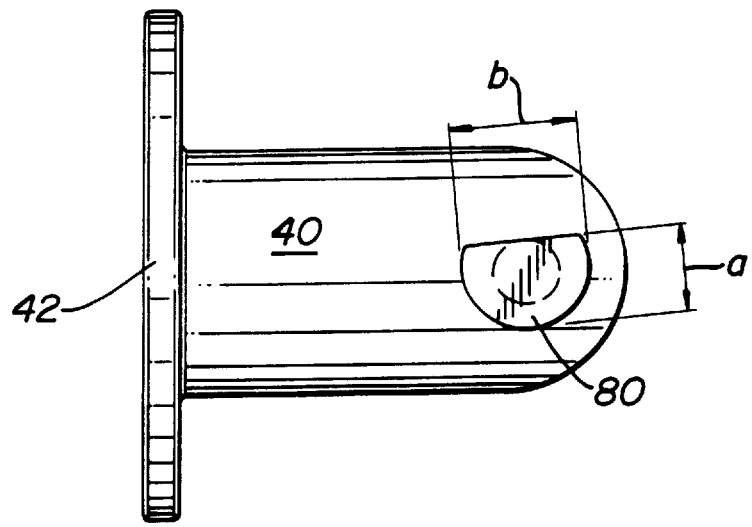
FIGS. 8A–8B are enlarged plan views of the locking stud of the quick release mechanism of the apparatus of FIG. 1 illustrating the reciprocal orientation of the locking flange portions on each side of the locking stud.
Figure 8B:
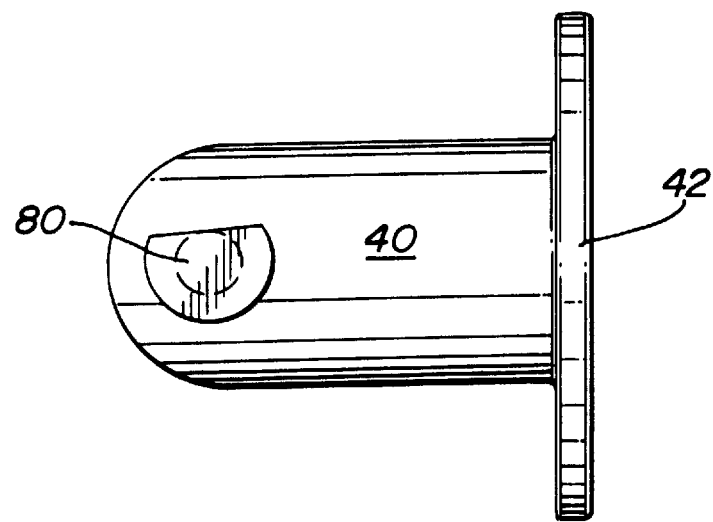

FIGS. 8A and 8B are side plan views of a single locking stud 40. As detailed in the Figures, flange 80 on a first side of locking stud 40 is angularly offset or rotated 180° relative to the opposed flange 80 on the second side of the locking stud. Such reciprocal orientation of the flanges 80 ensures that locking latch 44 and locking stud 40 are correctly reassembled so the latch 44 is in the proper orientation.

Referring now to FIGS. 9–10, instrument support member 66 may also be disassembled from wrist restraining member 18. Mounting pins 72 of instrument support member 66 have a semicircular shaped flange 86 similar in configuration to flange 80 of locking stud 40 of quick release mechanism 38. Similarly, upright posts 76 include a circumferential recess 88 and opposed release grooves portions 90 in their side surfaces which are similar to circumferential recess 82 and groove portions 84 of locking latch 44. Thus, in the mounted condition of instrument support member 66, mounting pins 72 are retained within circumferential recesses 88 by engagement of the semicircular shaped flange 86 with portions of upright member 76 defining the circumferential recess. To release instrument support member 66, the instrument support member 66 is pivoted upwardly as shown in FIG. 9 such that the portion of semicircular flange 86 having the smaller dimension is in alignment with the opposed release grooves 90. Thereafter, the instrument support member is removed by sliding flange 86 between the boundaries defined within the opposed grooves 90. FIG. 10 depicts instrument support member 66 disassembled from wrist restraining member 18. Note that similar to the flanges 80 of locking stud 40, the flanges 86 of support member 66 are angularly offset by 180° to ensure correct reassembly of support member 66 and wrist restraining member 18.

After removal of the wrist restraining member 66, the adjusting screw 78 is removed from member 66 and instrument holder 70 is slid off member 66 in the direction of arrow D.

After removal of all the locking latches 44, and restraining member 14, 16 and 18, support member 66, adjusting screw 78 and instrument holder 70, the apparatus 10 is in its fully disassembled condition with the component parts taken down to their basic elements and can then be sterilized. Sterilization of the apparatus is facilitated since the components are fully accessible to the sterilization fluids or gases. After sterilization, the apparatus may thereafter be reassembled to be used in subsequent surgical procedures.

Referring now to FIG. 11, there is illustrated a guiding instrument intended for use with apparatus 10 during carpal tunnel surgery. Guiding instrument or director 100 is intended to be inserted into the carpal tunnel to guide an instrument such as a balloon catheter into the tunnel. Guiding instrument 100 includes a handle 102 and an elongated member 104 extending distally from the handle 102. Handle 102 defines a depressed area 106 ergonomically dimensioned to be engaged by the thumb of the user and also possesses a longitudinal bore formed therein (not shown). Elongated member 104 consists of a proximal portion 108 having a substantially planar upper surface 110 and a distal end portion 112 having a flat distal tip 114 which frictionally receives end cap 103 which is adhesively secured to the balloon described below. An aperture 116 is formed in a wall of distal end portion 112.

Referring now to FIGS. 12–14, a catheter support 200 is shown for supporting a catheter to perform surgery in relieving the symptoms of carpal tunnel syndrome. Catheter support 200 includes frame 202. An elongated flexible catheter tube 204 is connected to the frame 202 in a manner described below. A flexible membrane 206 e.g. a balloon, is mounted at the distal end portion of the catheter tube 204. Preferably, the balloon and catheter are attached to the guiding instrument 100 during manufacturing and shipped as an integral unit. That is, distalmost tip 207 of catheter tube 204 and/or the distal edge of the balloon are bonded to end cap 103 of guiding instrument 100. Alternately, the catheter tube 204 and balloon can be sold as a separate unit and inserted into the guiding instrument by the user.

Referring to FIGS. 13–15, in conjunction with FIG. 12, frame 202 accommodates a syringe unit 208 having syringe housing 210 and plunger 212 at least partially disposed within the syringe housing 210. Frame 202 includes two half sections 202a, 202b which are attached along their respective peripheries by spot welding, adhesives or the like. Syringe housing 210 accommodates a supply of fluid such as saline which is dispensed through catheter tube 204 to inflate flexible membrane 206. Plunger 212 includes screw threads 214 which cooperate with threads 216 of frame 202. Accordingly, rotation of plunger 212 in a first direction causes distal axial movement of the plunger due to the cooperation of the engaged threads, to thereby dispense the fluid into flexible membrane 206. Rotation of plunger 212 in a second (reverse) direction causes proximal axial movement of the plunger and, consequently, deflation of flexible membrane 206. Thus, due to the provision of the threads of plunger 212 and frame 202, the surgeon may selectively incrementally control the inflation and deflation of flexible membrane 206. Plunger 212 includes a control knob 218 dimensioned to be grasped by the user to rotate the plunger 212.

Catheter support 200 also includes a pressure monitor gauge 220 in fluid communication with the interior of syringe housing 210 via T-connector 222 and tubes 223, 225 and luer lock 226 to monitor the fluid pressure being dispensed from the syringe housing 210. Pressure gauge 220 is advantageously angularly oriented to be readily viewed by the surgeon, i.e., the pressure gauge 220 is mounted on a portion of frame 202 which is angularly offset from the remaining portion of the frame.

Referring now to FIGS. 13–14, and particularly to FIG. 13, the connection of catheter tube 204 to syringe housing 210 will be discussed. Catheter tube 204 has a luer lock 205 positioned at its proximal end which connects to valve assembly 230 via male luer lock 232. A female luer lock 234 connects valve assembly 230 to tubing 236 via luer lock 238. Tube 236 is connected to T-connector 232. Catheter tube 104 is fabricated from a flexible material and includes openings at its distal end to allow passage of the inflation fluid into the flexible membrane 206. Flexible membrane is preferably fabricated from a polyester resin such as polyetheylene teraphthalate or other suitable material. Valve assembly 230 includes junction block 231 and check valve 233 to prevent overinflation of the flexible membrane 206. Check valve 224 may be any conventional valve capable of leaking fluid when the pressure in the catheter exceeds a predetermined value. Alternatively, a valve which shuts off the flow of fluid when the inflation pressure exceeds a predetermined valve could be provided.

In an alternate embodiment illustrated in FIG. 11A, the flexible membrane, e.g. balloon, can be welded directly to the guiding instrument 100' adjacent the aperture 116', and the channel in the guiding instrument itself could provide a passageway for the inflation fluid. This would eliminate the need for a separate catheter tube 204.

The use of apparatus 10 with guiding instrument 100, catheter housing 200 and catheter tube 204 for surgery to relieve the symptoms of carpal tunnel syndrome will now be described. Referring to FIG. 2, the patient's hand is placed prostrate on support surface 20 with the palm facing upwardly. Finger restraining member 14 is adjusted both longitudinally and vertically. The quick release mechanism is secured by moving locking latch 44 downwardly to thereby positively fix the finger restraining member 14 at the desired position. Thumb restraining member 16 and wrist restraining member 18 are likewise moved to the desired position to accommodate the patient's hand and are secured by rotation of locking latch 44 downwardly. Once in a fully secured position, guiding instrument 100, which has the catheter tube 104 fixed positioned inside so that flexible membrane 206 is adjacent aperture 216, is placed within a groove 68 formed in instrument support member 66 (as shown in FIG. 16) and positioned within a previously formed incision in the patient's wrist. Guiding instrument 100 may then be advanced to a location under the carpal tunnel ligament. Instrument holder 70 is slid over the guiding instrument 100 to enclose the device thereby maintaining the instrument 100 within the general confines of the groove. FIG. 17 illustrates the positioning of instrument holder 70 over guiding instrument 100. The planar upper surface 110 of guiding instrument 100 (FIG. 11) provides increased surface area to enhance frictional locking engagement of instrument holder 70 with the instrument 100. FIG. 18 illustrates, in side plan view, guiding instrument 100 positioned within the hand. Adjusting screw 78 is then rotated to pivot instrument support 66 in the direction of arrow D of FIG. 18, thus lifting the guiding instrument 100 towards the palm of the patient's hand to lift the ligament further from the underlying median nerve.

Figure 19:
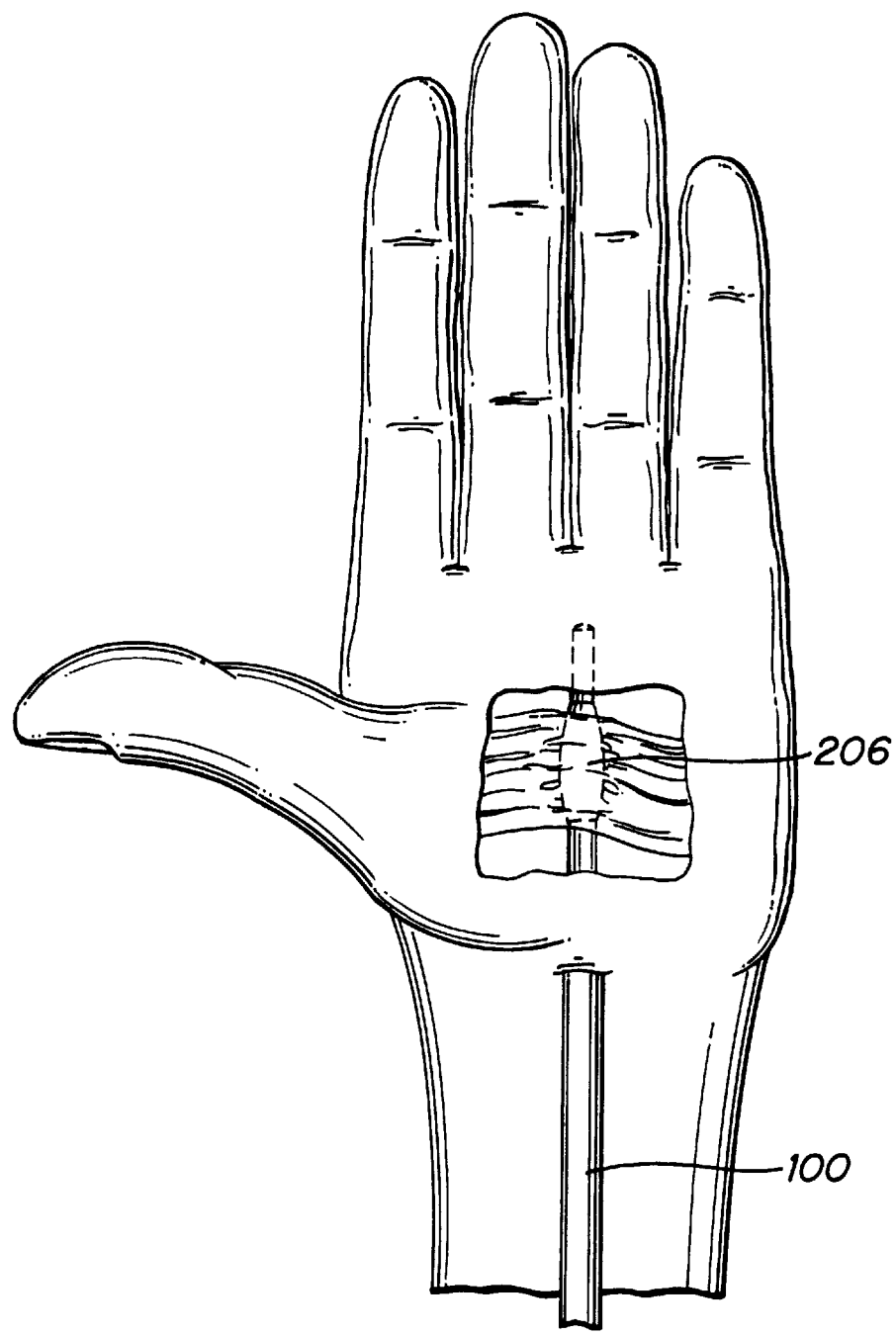
FIG. 19 is top plan view with portions cut away of the patient's hand illustrating the catheter positioned proximal the transverse carpal tunnel ligament to stretch the carpal ligament in accordance with the preferred method for treating carpal tunnel syndrome.

Control knob 218 of plunger 212 is rotated in a first direction to cause distal advancement of the plunger to dispense fluid through catheter tube 204 and into flexible membrane 206. Flexible membrane 206 inflates and expands through aperture 116 in the guiding instrument 100 to contact and stretch the transverse carpal ligament thereby relieving pressure off the median nerve. Note that aperture 116 is formed in only the top surface to allow expansion of the membrane in only the upward direction. This protects the underlying median nerve. FIG. 19 illustrates the positioning of flexible membrane 206 and guiding instrument 100 adjacent the carpal tunnel ligament. It is to be appreciated that the pressure of flexible membrane 206 is easily controlled through the screw threads of the plunger 212 and frame 210 as previously noted. Further, the fluid pressure during inflation can be monitored by the surgeon with pressure gauge 220. Preferably the desired pressure is approximately 150 psi, although clearly other pressures are contemplated. If pressure in the catheter 200 exceeds a predetermined valve, check valve 224 will relieve the pressure by leaking the fluid supply to flexible membrane 206, thus avoiding overinflation which could cause possible damage to the transverse carpal ligament or other bodily tissue within the tunnel. If a small flexible member is utilized, it can be moved, if desired, to engage distal and proximal regions of the ligament by simply advancing or retracting guiding instrument 100 or advancing or retracting the catheter housing 200.

While the above description contains many specifics, these specifics should not be construed as limitations on the scope of the invention, but merely as an exemplification of a preferred embodiment thereof. Those skilled in the art will envision other possible variations that are within the scope and spirit of the invention as defined by the claims appended hereto.

What is claimed is:

1. A method of performing carpal tunnel surgery comprising:

placing a patient's hand in a hand support having a finger restraint and a thumb restraint, and a latch mechanism associated with each of the finger and thumb restraints, the hand support including a supporting surface for supporting the patient's hand and defining a longitudinal axis and a vertical axis;

adjusting the finger and thumb restraints in a general longitudinal direction and a general vertical direction to accommodate the patient's hand;

securing the finger and thumb restraints in a desired position by adjusting the latch mechanisms associated therewith;

providing a catheter and a guiding instrument, the catheter having an inflatable balloon and a check valve in fluid communication therewith to prevent over inflation of the balloon, and a knob for inflating the inflatable balloon;

inserting the guiding instrument with the catheter supported thereby into an instrument support located on the hand restraint;

adjusting the angular orientation of the guiding instrument by adjusting the angular orientation of the instrument support; and rotating the knob to progressively inflate the balloon to stretch the carpal tunnel.

2. The method according to claim 1, further comprising the step of monitoring the pressure of the balloon.

3. The method according to claim 2, wherein the step of adjusting the latch mechanism includes the step of pivoting the latch member with respect to the restraints.

4. The method according to claim 1 further including the step of rotating the knob to deflate the balloon subsequent to the step of rotating the knob to progressively inflate.

5. The method according to claim 4 further including the step of adjusting the longitudinal orientation of the guiding instrument and catheter relative to the carpal tunnel.

6. The method according to claim 5 wherein the step of rotating the knob to progressively inflate is repeated subsequent to the step of adjusting.

7. The method according to claim 1 including the step of fixedly retaining the guiding instrument to the instrument support.

8. The method according to claim 7 wherein the step of retaining includes sliding a locking member mounted to the instrument support to a position in locking engagement with the guiding instrument.

9. The method according to claim 1 wherein the hand support includes a wrist restraint and further including the step of adjusting the wrist restraint to accommodate the patient's hand.

10. The method according to claim 9 further including the step of securing the wrist restraint in a desired position by adjusting a latch mechanism associated with the wrist restraint.

11. The method according to claim 1 wherein the step of adjusting the angular orientation of the guiding instrument includes rotating a set of screws mounted to the instrument support.

12. A method for performing carpal tunnel surgery, comprising the steps of:

providing a hand support including a supporting surface, a wrist securing member, an instrument support member mounted to the wrist securing member and an instrument locking member mounted to the instrument support member;

positioning a patient's hand in a prostate position on the supporting surface of the hand support;

moving the wrist securing member relative to the supporting surface to engage the patient's wrist;

positioning an expanding instrument at least partially within a groove defined in a surface of the instrument support member;

advancing the expanding instrument relative to the instrument support member to access the carpal tunnel ligament such that an expanding portion of the expanding instrument is adjacent the carpal tunnel ligament;

sliding the instrument locking member onto the expanding instrument to engage the instrument to thereby retain the expanding instrument at a fixed longitudinal position relative to the instrument support member; and actuating the expanding instrument to stretch the carpal tunnel ligament.

\* \* \* \* \*